United States Patent
Martin et al.

(10) Patent No.: US 6,752,759 B2
(45) Date of Patent: Jun. 22, 2004

(54) COOLED STABILIZER FOR SURGICAL PROCEDURES

(76) Inventors: Thomas E. Martin, 20 Waterview Ave., Riverside, RI (US) 02915; Michael A. Valerio, 44 Ray Rd., Wrentham, MA (US) 02093

( * ) Notice: Subject to any disclaimer, the term of this patent is extended or adjusted under 35 U.S.C. 154(b) by 171 days.

(21) Appl. No.: 10/113,793

(22) Filed: Apr. 1, 2002

(65) Prior Publication Data

US 2003/0187332 A1 Oct. 2, 2003

(51) Int. Cl.⁷ .............................. A61B 1/32; A61B 18/18; A61F 7/00
(52) U.S. Cl. ....................... 600/205; 600/228; 600/229; 606/23; 607/108
(58) Field of Search ................................ 600/205, 210, 600/228, 229, 37; 606/20, 21, 22, 23; 607/104, 105, 108, 114

(56) References Cited

U.S. PATENT DOCUMENTS

| | | | |
|---|---|---|---|
| 4,863,133 A | 9/1989 | Bonnell | |
| 4,971,056 A | 11/1990 | Seacord | |
| 5,057,117 A | 10/1991 | Atweh | |
| 5,117,822 A | * 6/1992 | Laghi | .......................... 604/27 |
| 5,150,706 A | 9/1992 | Cox et al. | |
| 5,513,827 A | 5/1996 | Michelson | |
| 5,730,757 A | 3/1998 | Benetti et al. | |
| 5,799,661 A | 9/1998 | Boyd et al. | |
| 5,836,311 A | 11/1998 | Borst et al. | |
| 5,875,782 A | 3/1999 | Ferrari et al. | |
| 5,894,843 A | 4/1999 | Benetti et al. | |
| 5,899,425 A | 5/1999 | Corey Jr. et al. | |
| 5,947,896 A | 9/1999 | Sherts et al. | |
| 6,015,382 A | 1/2000 | Zwart et al. | |
| 6,033,362 A | 3/2000 | Cohn | |
| 6,036,641 A | 3/2000 | Taylor et al. | |
| 6,063,021 A | 5/2000 | Hossain et al. | |
| 6,102,854 A | 8/2000 | Cartier et al. | |
| 6,231,506 B1 | 5/2001 | Hu et al. | |
| 6,306,085 B1 | 10/2001 | Farascioni | |
| 6,348,036 B1 | 2/2002 | Looney et al. | |
| 6,478,733 B1 | * 11/2002 | Weinstein et al. | .......... 600/213 |
| 2003/0060685 A1 | * 3/2003 | Houser et al. | .............. 600/206 |
| 2003/0060814 A1 | * 3/2003 | Capuano et al. | .............. 606/21 |
| 2003/0065372 A1 | * 4/2003 | D'Alessandro et al. | ..... 607/105 |

FOREIGN PATENT DOCUMENTS

| | | |
|---|---|---|
| EP | 0 993 806 | 4/2000 |
| WO | WO 00/10466 | 3/2000 |
| WO | WO 00/15119 | 3/2000 |
| WO | WO 00/62680 | 10/2000 |
| WO | WO 00/66008 | 11/2000 |
| WO | WO 01/03585 | 1/2001 |
| WO | WO 01/17437 | 3/2001 |
| WO | WO 01/58361 | 8/2001 |

OTHER PUBLICATIONS

D. Roux, et al. "New Helper Instrument in Cardiac Surgery" (1989).

* cited by examiner

*Primary Examiner*—Cary E. O'Connor
(74) *Attorney, Agent, or Firm*—Dechert, LLP; John W. Ryan

(57) ABSTRACT

A cooled stabilizer is provided for use in coronary bypass grafting surgical procedures. The cooled stabilizer can be attached to a surgical retractor for providing localized traction, stabilization and/or hemostasis to a predetermined area of body tissue. The stabilizer includes cooling channels and/or pads forming a continuous bottom surface for providing a chilled surface to contact body tissue. In one example, the cooled stabilizer can be shaped as a horseshoe with chilled surfaces over horseshoe sections and optionally over a heel.

41 Claims, 20 Drawing Sheets

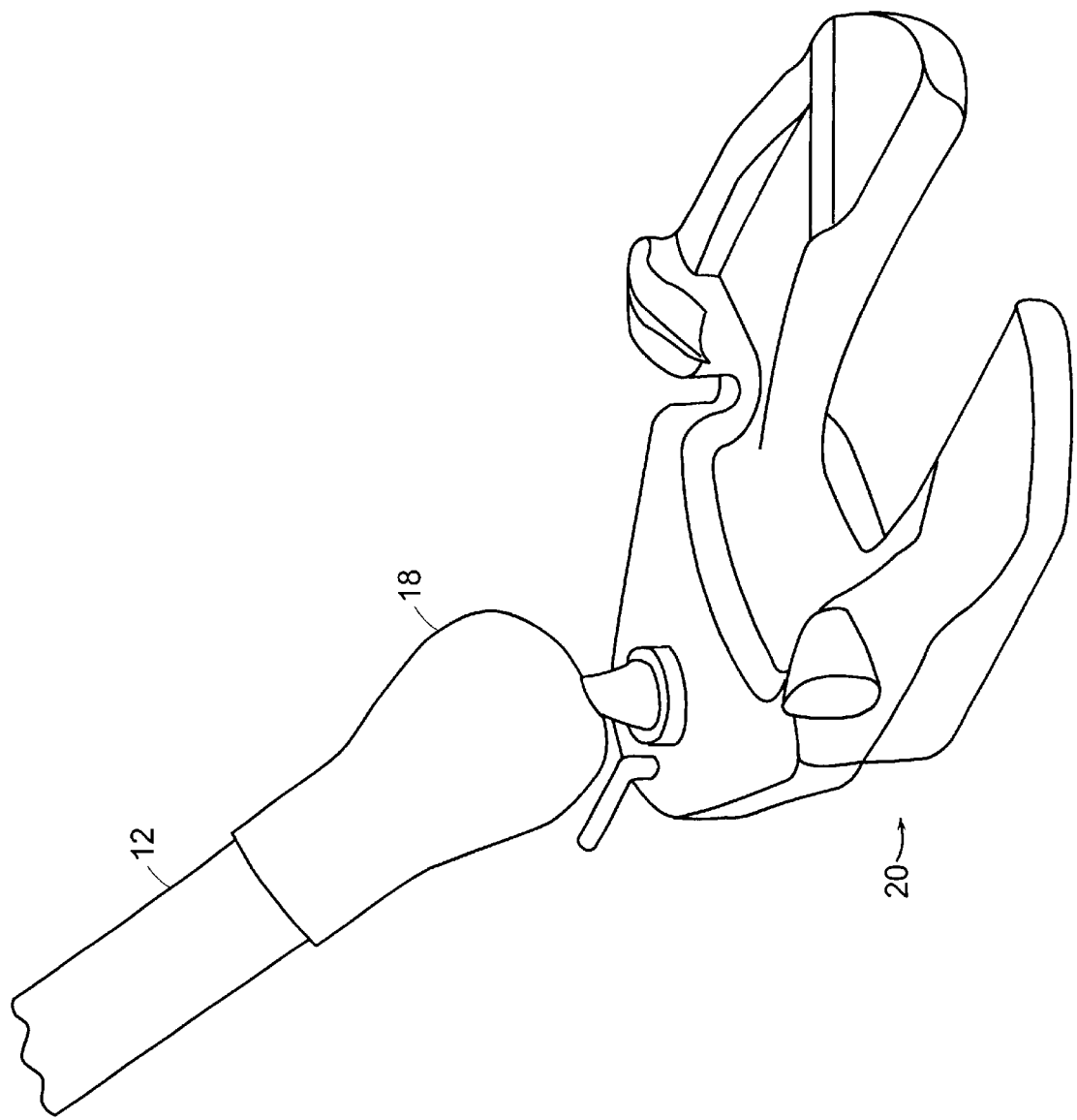

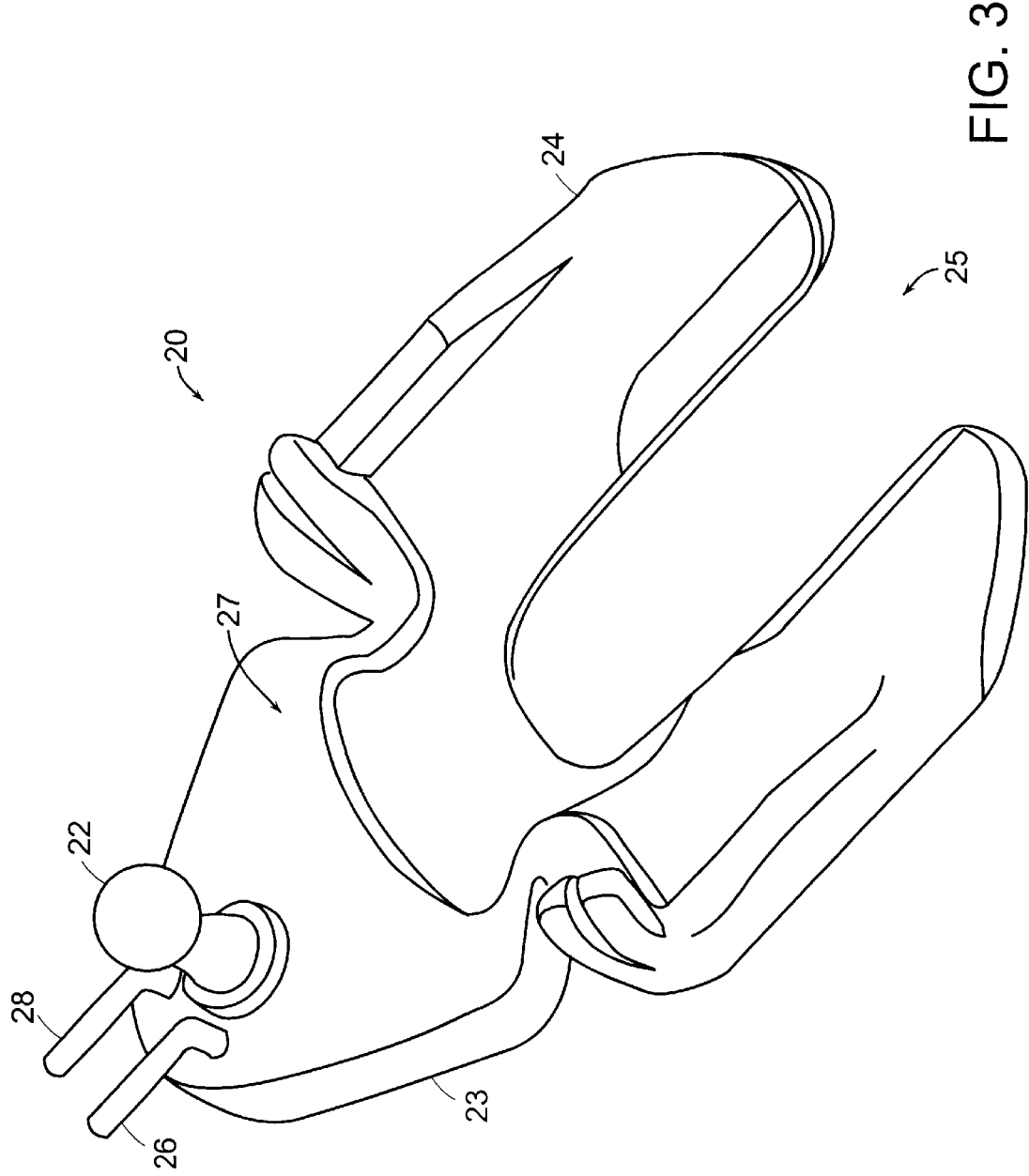

COOLED STABILIZER FOR SURGICAL PROCEDURES

FIELD OF INVENTION

The present invention relates to surgical retractors and devices for stabilizing a predetermined area of the body during a surgical procedure, more particularly to a stabilizer used in connection with a retractor that is preferably used in coronary artery bypass grafting surgical procedures, and more specifically to a cooled stabilizer attached to a rigid or flexible arm for providing a chilled stabilization surface in contact with body tissue.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system affecting blood flow to the heart.

One technique for treating such a blockage or restriction is a surgical procedure known as a coronary artery bypass graft (CABG) procedure, which is commonly performed while using a heart-lung machine ("on-pump"), but can also be performed without the heart-lung machine ("off-pump"). The surgical correction of occluded or stenosed coronary arteries by means of bypass grafting is among the most common procedures performed today, especially when multiple grafts are needed.

In the coronary artery bypass graft procedure, the surgeon either removes a portion of a vein or artery from another part of the body for grafting or detaches one end of a local artery, e.g., the left internal mammary artery (LIMA) or the right internal mammary artery (RIMA), and connects that end past the obstruction in the coronary artery while leaving the other end attached to the arterial supply. When using a vein or artery from another part of the body, the surgeon provides arterial supply from the aorta and connects to a point that bypasses the obstruction. In both cases, the objective is to bypass the obstruction and restore normal blood flow to the heart.

In addition, when using the on-pump CABG technique, the surgeon makes a long incision down the middle of the chest, saws through the sternum, spreads the two halves of the sternum apart and then performs the necessary procedures to connect the surgical patient to a cardiopulmonary bypass machine to continue the circulation of oxygenated blood to the rest of the body while the heart is stopped and the graft is being sewn in place. Although such a procedure is one common technique for treatment, the procedure is lengthy, traumatic, costly and can damage the heart, the central nervous system, and the blood supply.

Interventional techniques, such as percutaneous transluminal angioplasty (PTCA), have gained popularity as an alternative method of therapy for atherosclerosis. PTCA is a minimally invasive technique that subjects the patient to reduced trauma and reduced recovery time, especially when compared to on-pump CABG techniques.

Although PTCA procedures are often successful, complications can arise, such as restenosis or thrombosis and embolism. Restenosed vessels often require surgical intervention for correction. The surgical correction of restenosis, like the conventional coronary bypass surgical procedure, previously required the heart to be stopped and the patient placed on heart/lung bypass.

In recent years, and in an effort to reduce cost, risk, and trauma to the patient, physicians have turned to minimally or less invasive surgical approaches to the heart bypass procedure, such as intercostal and endoscopic access to the surgical site. With such off-pump CABG procedures, the heart is beating during the surgical procedure. Thus, there is no need for any form of cardiopulmonary bypass, and there is no need to perform the extensive surgical procedures necessary to connect the patient to such a bypass machine.

Such attempts at performing minimally invasive bypass grafting on a beating heart, however, have been characterized as tedious, dangerous and difficult because of the delicate nature of the surgical procedure, the lack of adequate access to the coronary vessels, and the lack of an ability to adequately stabilize and reduce tissue movement at the graft site. Because these procedures are performed while the heart continues to beat, the blood continues flowing and the heart continues moving in three-dimensional movement while the surgeon attempts to sew the graft in place.

There is disclosed in U.S. Pat. No. 6,348,036 to Looney et al. a surgical retractor and a tissue stabilization device for locally stabilizing a predetermined area of the body. The retractor includes a rail system having two arms and a rack segment interconnecting the two arms for maintaining a desired spacing therebetween. A stabilization arm having a handle segment connects the retractor with the stabilization device. The handle segment is attachable to the retractor by a connector such as a mounting mechanism or a sled member. The stabilization device is pivotally retained at a distal end of the stabilization arm. A bottom surface of the stabilization device can include a textured surface to facilitate engagement with tissue at the predetermined area.

There also is disclosed in U.S. Pat. No. 6,102,854 to Cartier et al. a sternal retractor including a rack bar and two arms attached to rails, and an arm mounted on the rails. A "contacting means" or stabilizer includes two parallel contacting arms that define an area where a targeted artery is engaged between the arms. Silastic tapes can be wrapped around the targeted artery, thereby restricting blood flow in the arterial window.

There also is disclosed in U.S. Pat. No. 5,730,757 an access platform for the dissection of an internal mammary artery. The described access platform has first and second blades interconnected to a spreader member that laterally drives the blades apart or together, and support pads interconnected to the first blade. A torsional member is operably interconnected to the first blade and the spreader member, and is used to vertically displace the first blade in either direction, thus increasing the surgeon's working space and visual access for dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 6,306,085 granted to Farascioni; U.S. Pat. No. 6,036,641 to Taylor et al.; U.S. Pat. No. 5,875,782 granted to Ferrari et al.; U.S. Pat. No. 6,033,362 granted to Cohn; U.S. Pat. No. 6,102,854 granted to Cartier et al.; U.S. Pat. No. 5,894,843 granted to Benetti et al.; European Application EP 0 993 806; PCT Publication WO 01/17437; PCT Publication WO 00/62680; and PCT Publication WO 01/58361 various devices for stabilizing a predetermined area on the heart or other organ of a patient, e.g., to enable a surgical procedure on the beating heart. Some of these devices include a stabilizer attached to an elongated arm, which can be movably attached to a rib retractor so that a person is not required to hold the arm. However, none of these devices disclose a chilled surface in contact with the heart for providing traction and quiescence, and that are capable of inducing hemostasis in a targeted area of tissue.

One example of a device for cooling the heart is U.S. Pat. No. 5,117,822 to Laghi, which discloses a spoon-like device including a handle part and a cradling part. The cradling part conforms to the shape of the human heart and serves to separate the heart from the walls of the thoracic cavity. Chilled saline solution is pumped through a passageway in the handle and seeps out through perforations onto the heart itself. Most of the saline solution forms a puddle in the thoracic cavity and is aspirated by a vacuum manifold.

Another example of a device for cooling the heart is provided in U.S. Pat. No. 5,799,661 to Boyd et al., which discloses a topical hypothermia device (see FIGS. 42–47) including a flexible heat exchanger with a passage for circulating cooling fluid. In use, the heat exchanger is filled with fluid and placed against the heart in contact with the myocardium. A pump forces cooling fluid from an outside reservoir into the device and through the passage of the heat exchanger. The reservoir can be cooled by an ice bath to provide cooling fluid of 0–4° C.

However, the prior art does not disclose a device that provides for traction, quiescence, or is capable of inducing hemostasis on a targeted area of the heart adjacent a grafting site. Further, none of these prior art devices are configured to be attached to an elongated arm for use with a surgical retractor.

It is therefore desirable to provide a cooled stabilizer device and system for providing traction and quiescence, and that can be capable of inducing hemostasis in a predetermined area of an organ such as the heart, and methods for using such a device.

SUMMARY OF THE INVENTION

The present invention features a system for retracting, manipulating, and stabilizing a predetermined area of the body. The system includes a stabilizer device having a chilled surface which provides traction and quiescence, and that can be capable of inducing hemostasis in a localized area of an organ such as the heart, and methods of use related thereto.

The cooled stabilizer and related devices and apparatuses that are featured herein are particularly advantageous for use in performing off-pump coronary artery bypass grafting (CABG) procedures in which the heart remains beating during the surgical procedure and/or other surgery in which the heart is stopped. One advantage of the present invention relates to the versatile use of the cooled stabilizer which is connected to an elongated arm and any location along the arms of a retractor or a rack portion thereof, and which can be manipulated to a desired position over an organ such as the heart. Additionally, the arm with cooled stabilizer of the present invention allows for a full range of three-dimensional motion which is controlled by a single knob that is spaced apart from each of the retractor and the arm. The cooled stabilizer is pivotable on an end of the arm by a ball-and-socket or other known joint.

The general shape of the cooled stabilizer can resemble devices of the type commonly known as the Cohn Cardiac Stabilizer or the Immobilizer marketed by the Genzyme Corporation of Cambridge, Mass. The preferred form of the stabilizer is a generally horseshoe shaped member having a planar surface with a centrally located opening therein that may or may not include a removable end piece thereon. Other suitable forms include square, rectangular, or teardrop shaped members. The central opening or window area is an area through which the surgeon performs the anastomosis or other procedure on the tissue of the beating heart. One form of the stabilizer is a multiple piece member so that once the anastomosis is completed, the pieces or an end portion thereof may be separated to remove the device from around the anastomosis.

Optionally, flexible tapes such as silastic tapes can be sutured through the tissue and then threaded around and connected to the stabilizer to provide temporary vessel occlusion by capturing the tissue and adjacent blood vessel against the bottom surface of the stabilizer. Once the stabilizer is positioned in the desired orientation and location in contact with the tissue, the flexible tapes are then pulled snug through the opening of the stabilizer to provide localized stabilization through both compression and traction forces on the artery or tissue.

A cooled stabilizer according to the present invention can include an insulated upper surface and a thermally conductive bottom surface having one or more channels, the channels circulating a fluid, preferably a cooling fluid to provide traction and quiescence to the adjacent tissue, and being capable of inducing localized hemostasis on a targeted area of body tissue and/or an artery. As used herein, the term "channel" refers to, for example, a line, a conduit, a tube, or space formed within the stabilizer that is capable of transmitting fluid along a path.

The cooled stabilizer includes one or more members, preferably two members, surrounding the targeted area adjacent a graft site. The bottom surface or a portion thereof of each of the members can be a thermally conductive surface for transferring the effects of the cooled fluid in contact with the targeted area on an organ, e.g., the heart.

The channels can be formed in one or more loops and include at least one inlet and one outlet, the inlet and outlet preferably elevated above the upper surface of the stabilizer. A preferred form of the stabilizer is in the shape of a horseshoe, with a thermally conductive surface provided on the bottom surface of the two members, or horseshoe sections of the horseshoe, and optionally including a heel being either a conductive surface or an insulating surface. If desired, the heel can be omitted and a differently shaped stabilizer can be provided, such as one having two or more parallel members. In any of these designs, it is desired to provide sufficient contact surface to cool the tissue adjacent to the targeted area to thereby reduce movement of the tissue.

The channels preferably are made integral with the bottom surface of the stabilizer. For example, the channels or tubes can be welded to the bottom surface. Alternatively, the tubes can be formed within plates having outer surfaces which serve as the upper and bottom surfaces of the stabilizer. The bottom surfaces in the heel and horseshoe sections preferably are made of biocompatible materials or surface treated with biocompatible materials. The tubes can circulate cooling fluid having a temperature of between approximately −30° C. and 10° C., or more preferably approximately −20° C. and 0° C., and still more preferably approximately −10° C. to 0° C.

In one example of the present invention, the channels are positioned around a periphery of the bottom surface of the stabilizer members (i.e. horseshoe sections) for distributing cooling fluid over a large area thereof. In another example, the bottom surface of the horseshoe sections can be a thermally conductive surface formed with one or more pads for providing traction and having an approximately constant temperature distribution over the surface of the pads. The pads can be positioned directly over the channels or can encompass a larger surface area, e.g., covering substantially the entire bottom surface of the horseshoe sections. In yet another example, the channels can be milled into plates for circulating fluid through the plates.

In a horseshoe configuration, the heel can include a flat bottom surface continuous with the bottom surface of the horseshoe sections, or alternatively can include a depressed or a raised portion, depending on whether minimized compression or additional compression, respectively, is to be imparted to the coronary artery and body tissue therearound.

In a further example of the cooled stabilizer of the present invention, a plurality of members can be arranged approximately parallel to each other around a targeted area of the epicardium. A surgeon can operate in a window of reduced movement tissue located between the members. Preferably the members include thermally conductive bottom surfaces and upper surfaces that can be conductive or insulative, the upper surfaces being linked together by a connecting member.

Other aspects and examples of the invention are more fully discussed below.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein:

FIG. 2B is a sectional, perspective view of the cooled stabilizer and arm of FIG. 2A;

FIG. 3 is a top perspective view of the cooled stabilizer of FIG. 2;

DETAILED DESCRIPTION OF THE INVENTION

Figure 1:
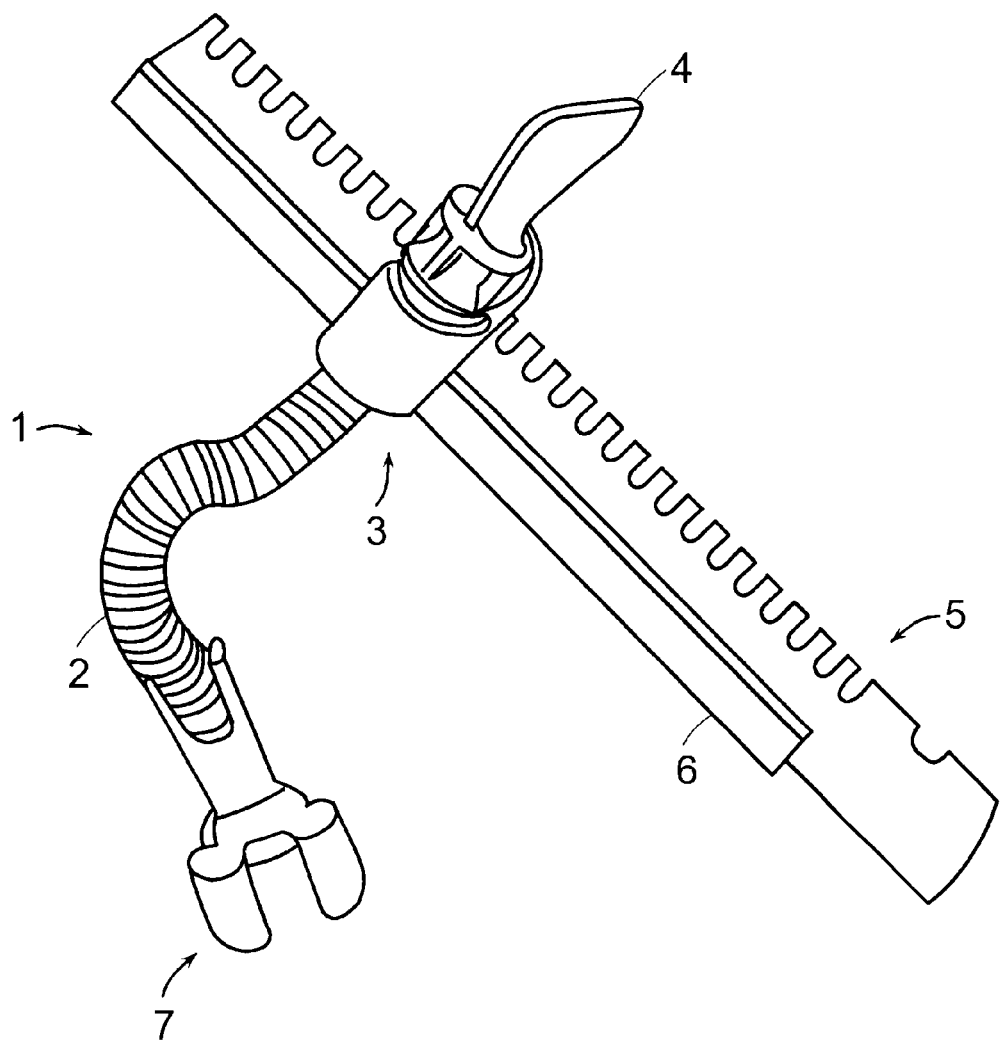
FIG. 1 is a perspective view of an exemplary cooled stabilizer according to the present invention attached to a flexible arm that is mounted on a section of a retractor.

FIG. 1 illustrates a device 1 capable of presenting a chilled surface for contact with body tissue according to the present invention, the device including a cooled stabilizer 7 attached to a distal end of a flexible arm 2, the arm being made up of a plurality of individually movable segments. A mounting assembly 3 is positioned at a proximal end of the arm for connecting the arm 2 to a retractor 5 in a known manner. As shown, the arm is positioned along a rail 6 of the retractor 5. Although only a section of the retractor 5 is shown in FIG. 1, it is known to position an arm at a plurality of locations along the arms and interconnecting segment of the retractor. The arm 2 depicted in FIG. 1 is a flexible arm, but a rigid arm can be substituted for the flexible arm 2, as is known in the art. A tightening assembly 4 is provided at the proximal end of the mounting assembly for tightening the segments of the arm 2 and thus fixing the cooled stabilizer 7 over a targeted area for forming a graft (not shown). A suitable flexible arm is disclosed in U.S. Ser. No. 10/008,509, which is incorporated by reference herein.

Figure 2A:
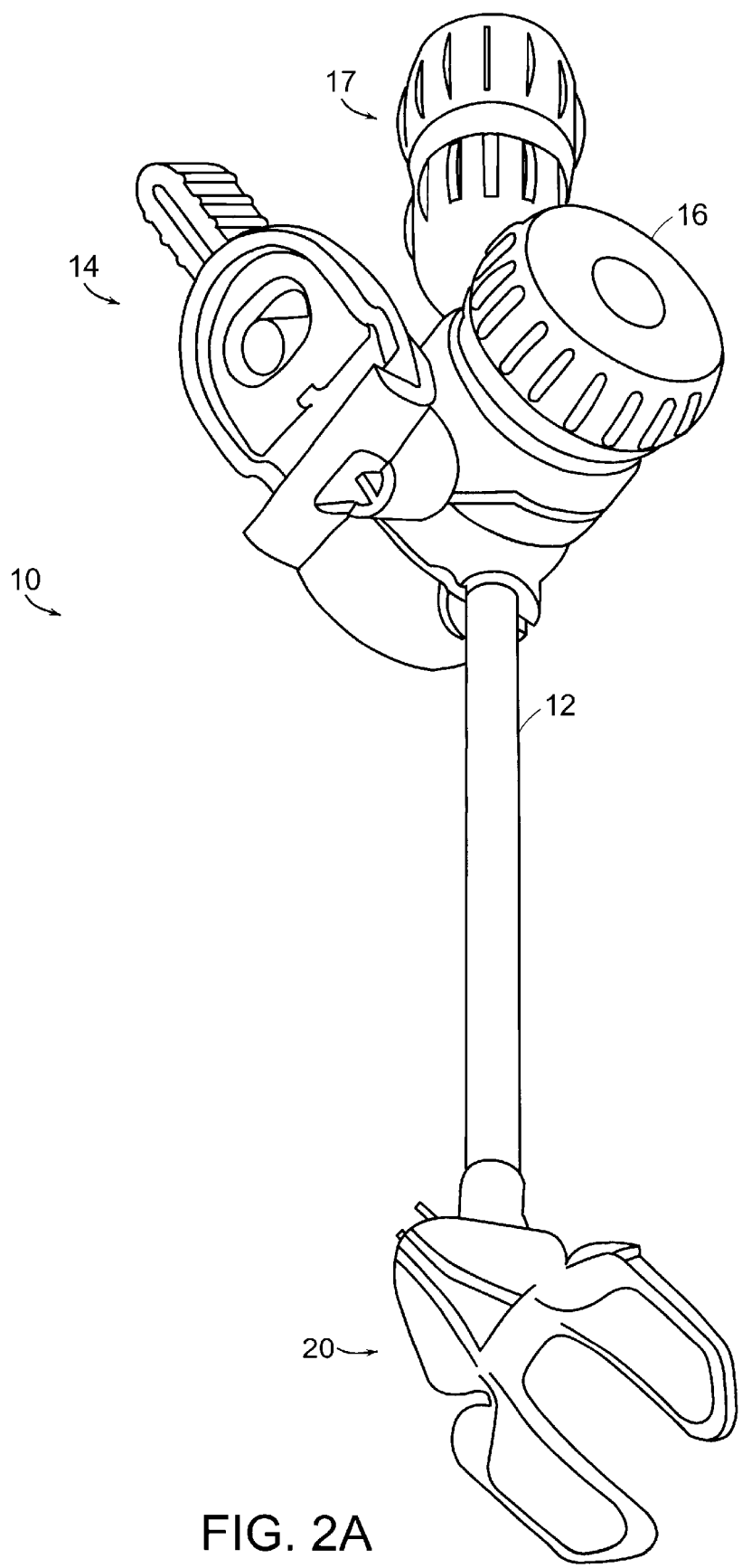
FIG. 2A is a perspective view of another exemplary cooled stabilizer attached to a rigid arm for connecting to a retractor.

FIGS. 2A and 2B are perspective views of a device 10 for presenting a chilled surface for contact with body tissue, the device including a cooled stabilizer 20 attached to an arm 12 which can be connected to a retractor in a known manner. For example, the arm can include a known mounting assembly 14, e.g., a cam and lever system for adjustably connecting the arm at any suitable position along the retractor. The arm 12 can be a rigid arm (as shown in FIG. 2A) or a flexible arm, as described with reference to FIG. 1. The stabilizer 20 can be pivotally attached to a distal end of the arm by a ball-and-socket joint or similar known attachment mechanism. An adjustment mechanism 16 and 17 such as conventional knobs can be used to position the stabilizer 20 in a desired position relative to body tissue and the retractor.

As shown in FIGS. 2B and 3, a distal end 18 of the arm 12 includes a socket joint for receiving a ball 22 of the stabilizer 20. Alternatively, a different type of attachment mechanism can be provided. One preferred form of the stabilizer 20 is a generally horseshoe shaped structure having first and second horseshoe sections 24, a central opening 25 positioned between the horseshoe sections, and optionally provided with a heel 27. Other shapes and forms of stabilizers are suitable, so long as at least one member is provided for receiving channels and imparting a chilled surface to body tissue.

In the cooled stabilizer of the present invention, fluid is circulated through channels in one or more members of the stabilizer, such that at least a portion of the bottom surface of one or more of the members can be chilled, thereby presenting a chilled surface for contact with body tissue. The chilled surface can provide localized traction and quiescence, and can be capable of inducing hemostasis in a predetermined area of the tissue.

As shown in FIG. 3, connections such as an inlet 26 and an outlet 28 carrying cooling fluid preferably are positioned above an upper surface 27 of the stabilizer. The inlet and outlet can be elevated above the upper surface 27 to prevent interference with tissue upon which the stabilizer is situated (see also FIG. 5). The inlet 26 and outlet 28 can be reversed in orientation if desired. In another possible modification, connections 26 and 28 can receive multiple channels, and thus each connection can serve as both an inlet and an outlet. The upper surface 27 can include at least one insulating layer to prevent the upper surface from becoming chilled, thereby protecting the graft as it is sewn in place and preventing the unnecessary loss of cooling from the fluid.

Figure 4:
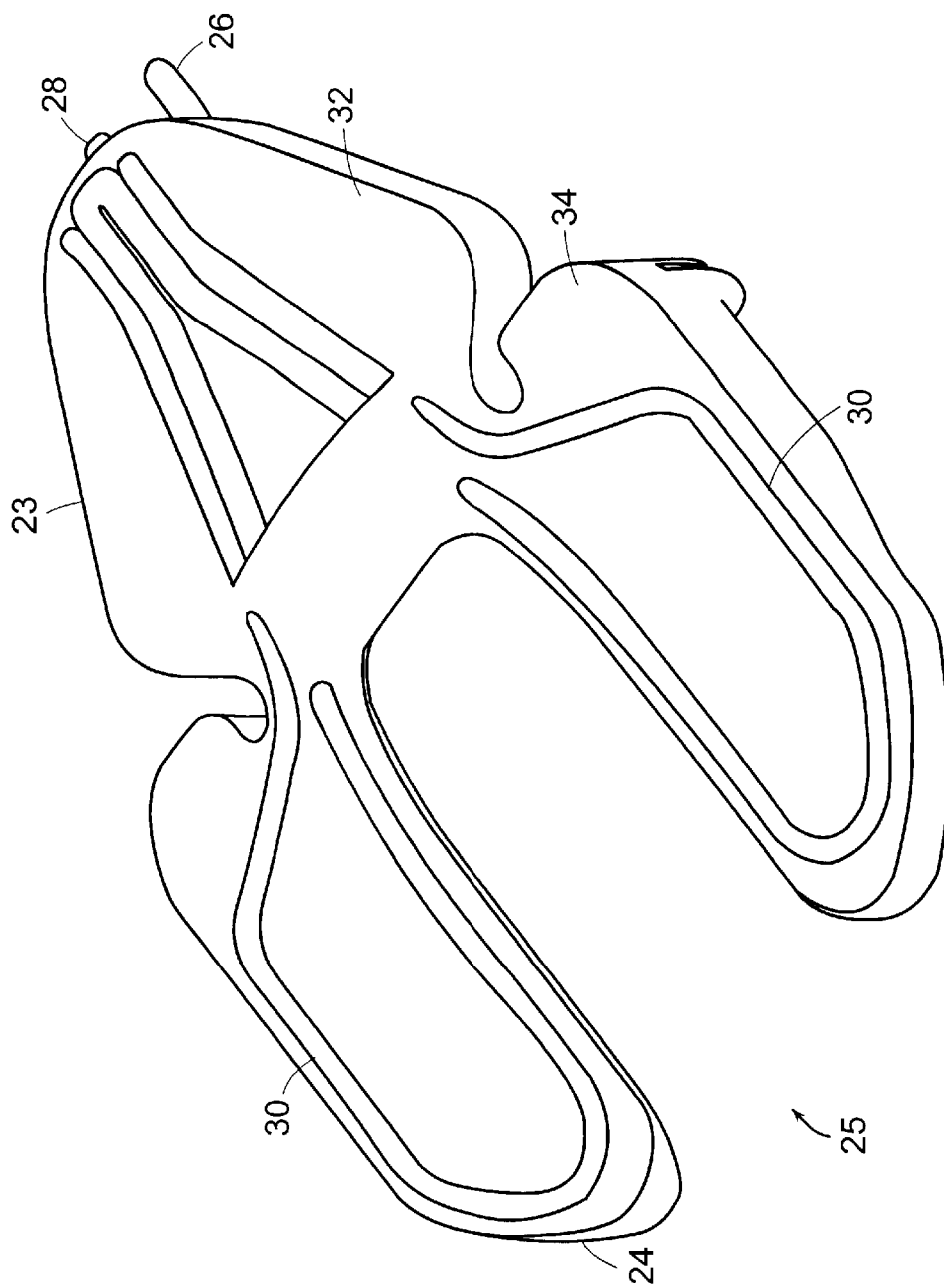
FIG. 4 is a bottom perspective view of the cooled stabilizer of FIG. 3.

FIG. 4 illustrates a bottom view of the cooled stabilizer, including one or more channels 30 connected to the inlet 26 and outlet 28 for circulating fluid through the stabilizer, the channels 30 preferably integrated into the heel 23 and horseshoe sections 24 to form a flat, planar bottom surface. The bottom surface includes surfaces 32 and 34 in the heel and horseshoe sections, respectively, which can be made integral with the channels 30. For example, the channels 30 can be welded to the bottom surface of the stabilizer. As used herein, channels 30 refer to a single channel, or alternatively, to a plurality of channels which are connected together or operate complimentary to one another. The upper surface 27 and bottom surface can be formed on complimentary plates which are joined together to form the stabilizer.

The bottom surfaces 34 of the horseshoe sections preferably are thermally conductive and can be made of metal or any other suitable material. Preferred materials include biocompatible materials such as stainless steel, gold, or silver. Also preferred are non-biocompatible materials that are surface treated, e.g., copper or aluminum which can be coated with a thin polymer coating, where the polymer coating is sufficiently thin so that it does not function as an insulator, or treated, as in plated, with an inert metal such as gold or silver.

Figure 5:
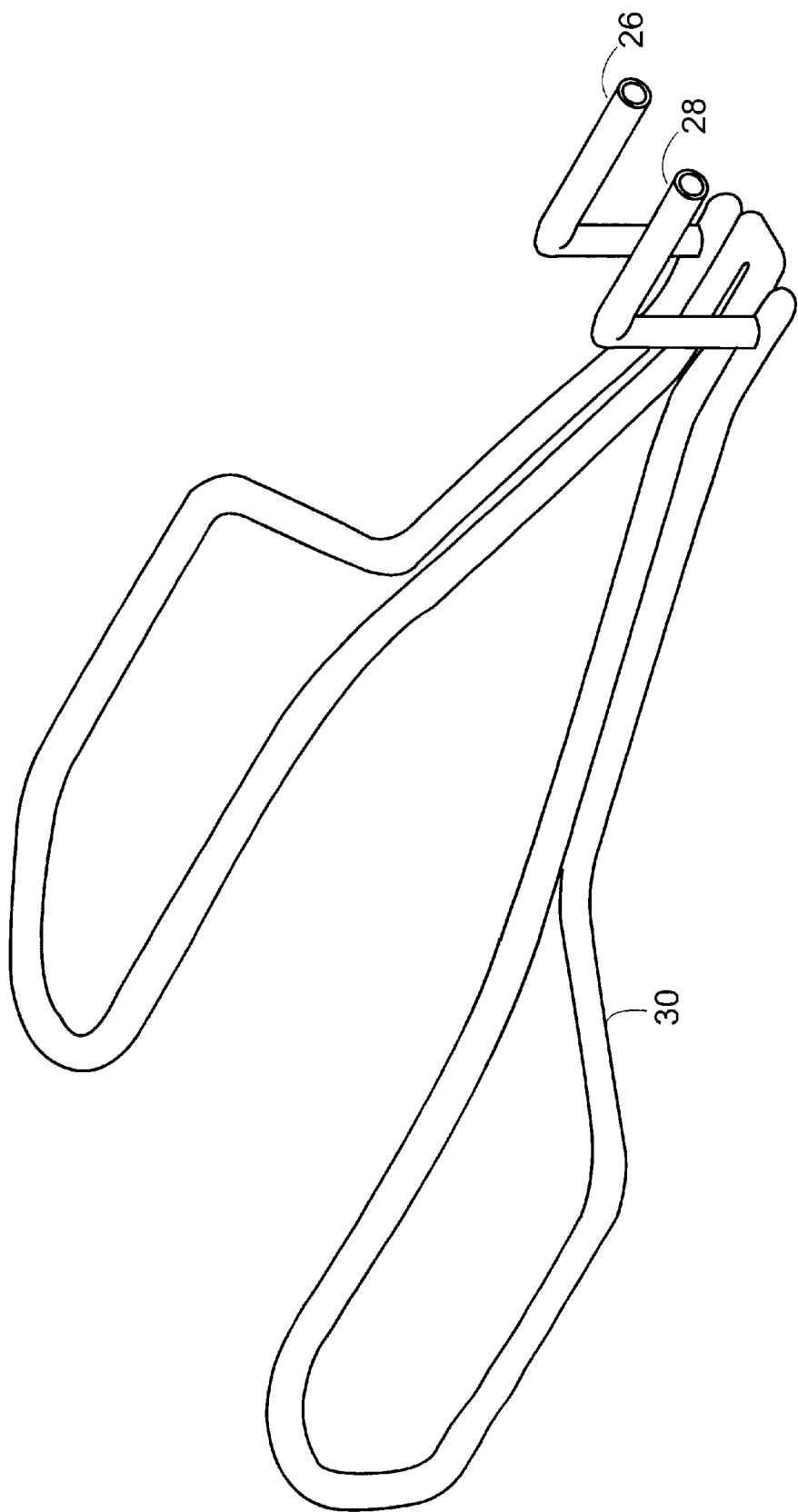
FIG. 5 is a perspective view of an arrangement of channels formed by tubing in the cooled stabilizer of FIG. 3.

The channels 30 can be made of a thermally conductive material similar to the bottom surface of the stabilizer, such as one or more of the materials discussed above. In the example of FIGS. 4 and 5, the channels 30 are positioned along the periphery of the horseshoe sections 24 to distribute fluid over a wide area encompassing substantially the entire bottom surface of the horseshoe sections. A chilled surface optionally can be provided on the bottom surface (underside) of the heel if desired, where the heel can be made of a thermally conductive material compatible with and preferably the same as the material(s) previously discussed. Alternatively, the underside of the heel can be covered with an insulating surface (not shown), in which case the channels 30 are buried beneath the insulating surface, and a chilled surface is exposed to body tissue only in the horseshoe sections 24.

The channels 30 can be configured to circulate cooling fluid having a temperature of between approximately −30° C. and 10° C., more preferably a temperature of between approximately −20° C. and 0° C., and still more preferably approximately −10° C. to 0° C. Preferably the cooling fluid is a saline solution, and can be chilled to approximately −10° C. or less before it enters the stabilizer, although other known cooling fluids such as alcohol or a saline-alcohol mixture can be used. Cooling fluid can be circulated in a closed-loop system or an open-loop system in a known manner. An example of one such system (not shown) involves use of a conventional pump and controller for regulating the velocity at which cooling fluid circulates through the system and the temperature of the cooling fluid. A conventional ice bath, chiller, or other cooling mechanism can provide suitable cooling. Further, a feedback loop to the controller can be included for adjusting the temperature and flow rate of the cooling fluid. After a surgical operation is completed, another fluid can be circulated through the channels 30. For example, a fluid having a temperature above the temperature of cooling fluid (e.g. a warmer saline solution) can be circulated through the channels 30 in order to help release the stabilizer from the graft area.

As discussed earlier, the bottom surface of the stabilizer can impart a chilled surface for contact with body tissue, the temperature of the chilled surface being regulated to an optimum temperature for tissue quiescence at a targeted surface and/or providing a generally uniform temperature. When the heel is provided as a chilled surface, preferably tissue quiescence and stability as well as hemostasis can be induced either by cooling alone or in conjunction with compression forces exerted by the heel. Alternatively, a relief on the heel can avoid compression of the coronary artery (see FIG. 8, and discussion below) and/or the heel can be insulated in order to avoid histological side effects of application of a cold surface to the coronary artery (see, e.g., FIG. 10).

Figure 6:
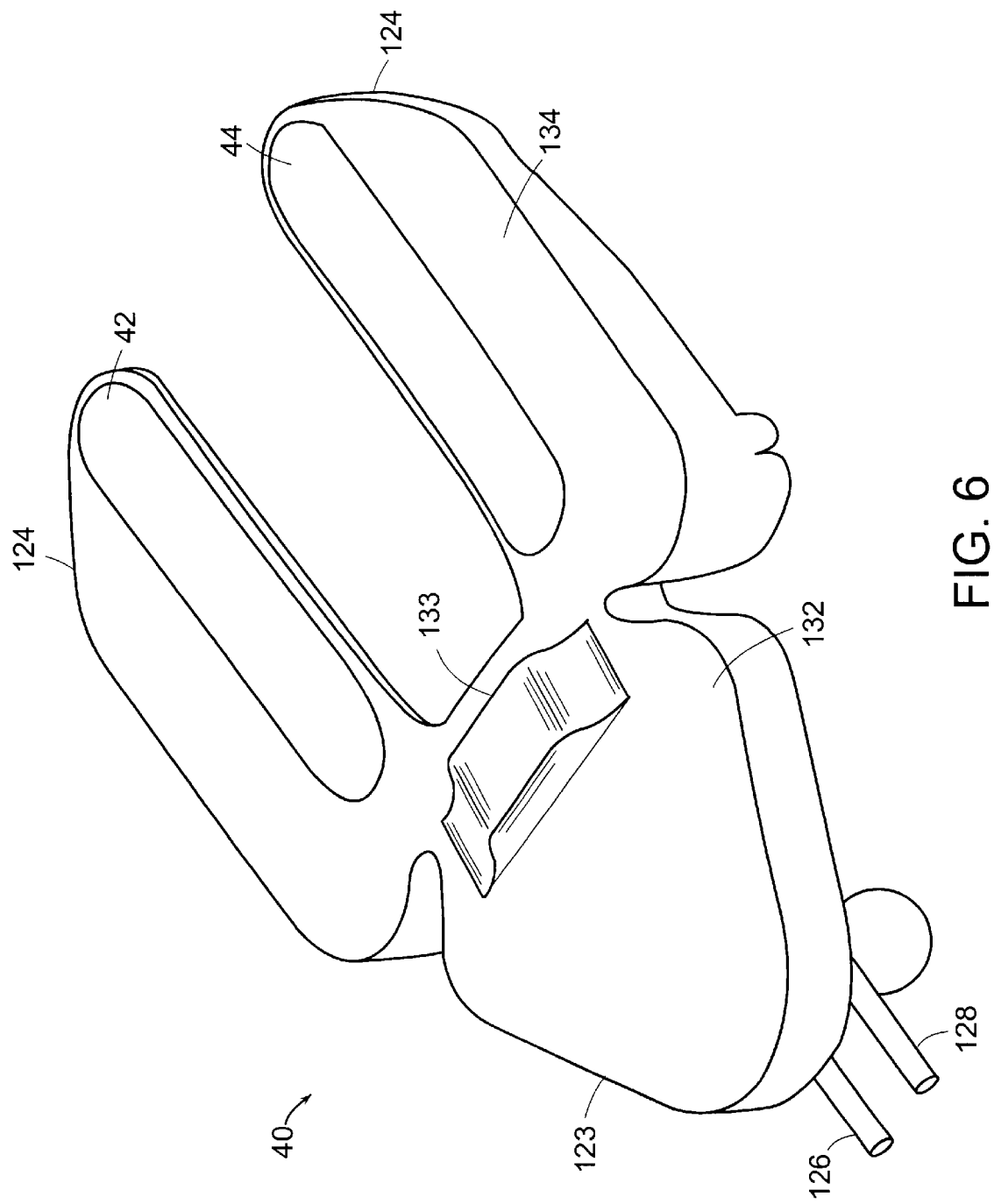
FIG. 6 is a bottom perspective view of another example of a cooled stabilizer according to the present invention.
Figure 7:
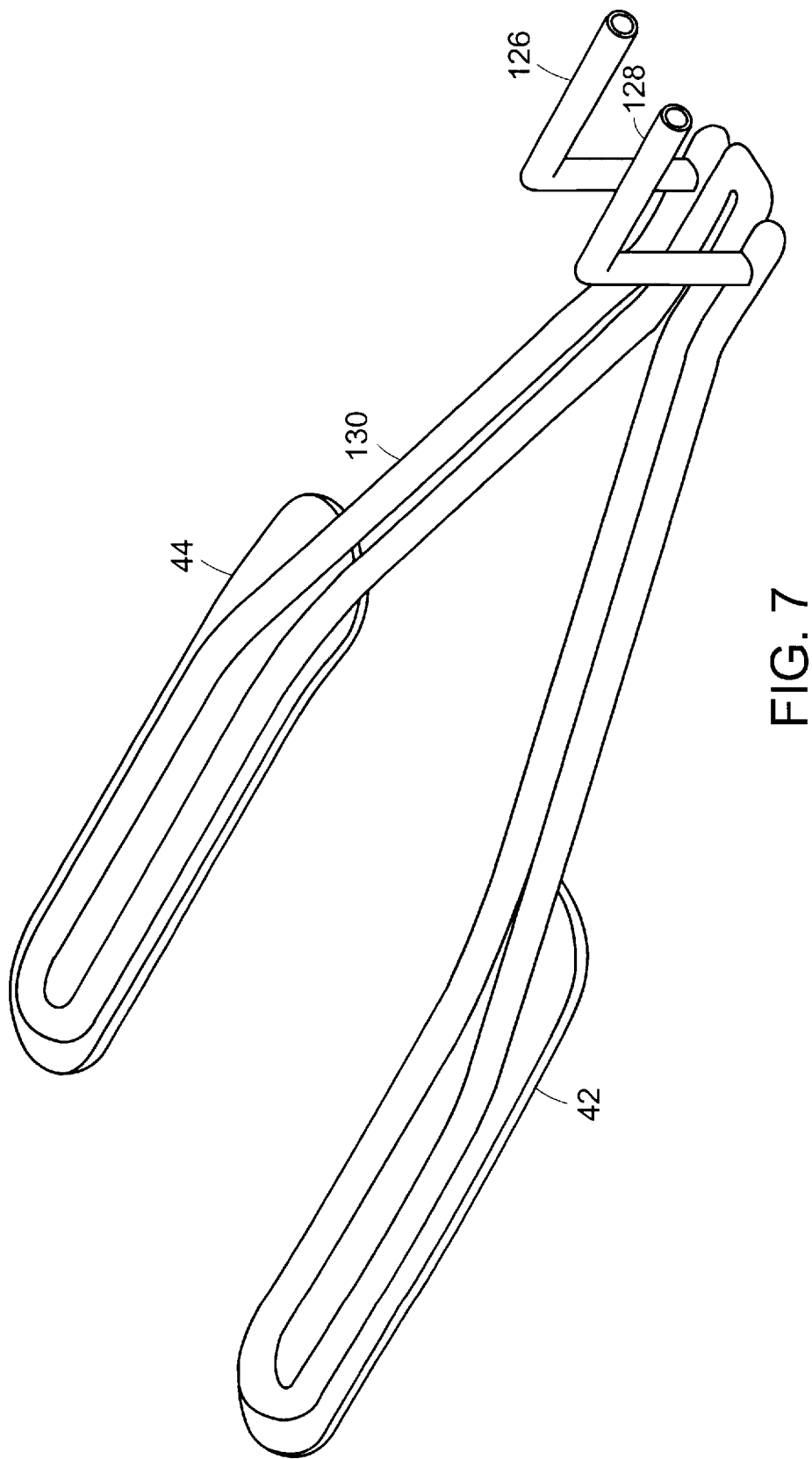
FIG. 7 is a perspective view of an arrangement of channels and pads in the cooled stabilizer of FIG. 6.

A further exemplary embodiment of the stabilizer of the present invention is shown in FIGS. 6 and 7. The stabilizer 40 of FIG. 6 is similar to that depicted in FIG. 4, where like reference numerals from FIG. 4 have been duplicated while being preceded by a "1". Therefore, the stabilizer 40 of FIG. 6 includes a heel 123 and horseshoe sections 124 (similar to heel 23 and horseshoe sections 24 of FIG. 4). Inlet 126 and outlet 128 preferably are elevated to an upper surface (not shown) of the stabilizer. A bottom surface of the stabilizer includes surfaces 132 and 134 in the heel and horseshoe sections, respectively, as well as a downwardly extending compression surface 133 that is oriented generally perpendicular to the horseshoe sections 124. In this exemplary embodiment, the bottom surface 132 of the heel is provided as an insulated surface, although a thermally conductive surface could be substituted therefore. Alternatively, the compression surface 133 may also be provided as an additional cooling surface.

As shown in FIGS. 6 and 7, one or more thermally conductive pads 42 and 44 are provided in contact with the channels 130. The channels 130 preferably are buried underneath the bottom surface of the stabilizer. The pads 42, 44 can be integrated into the bottom surface 134 to maintain a flat, planar surface in the vicinity of the horseshoe sections of the stabilizer, thereby providing substantially continuous cooling over the entire surface of the pads for contact with body tissue. The pads can be made of a suitable thermally conductive material, as discussed earlier, e.g., the same material as that which constitutes the bottom surface 134. The pads 42, 44 can include a textured surface to provide traction in the targeted area adjacent the graft. The pads can be made integral with the cooling channel 130 and the bottom surface 134 in a known manner.

Figure 8:
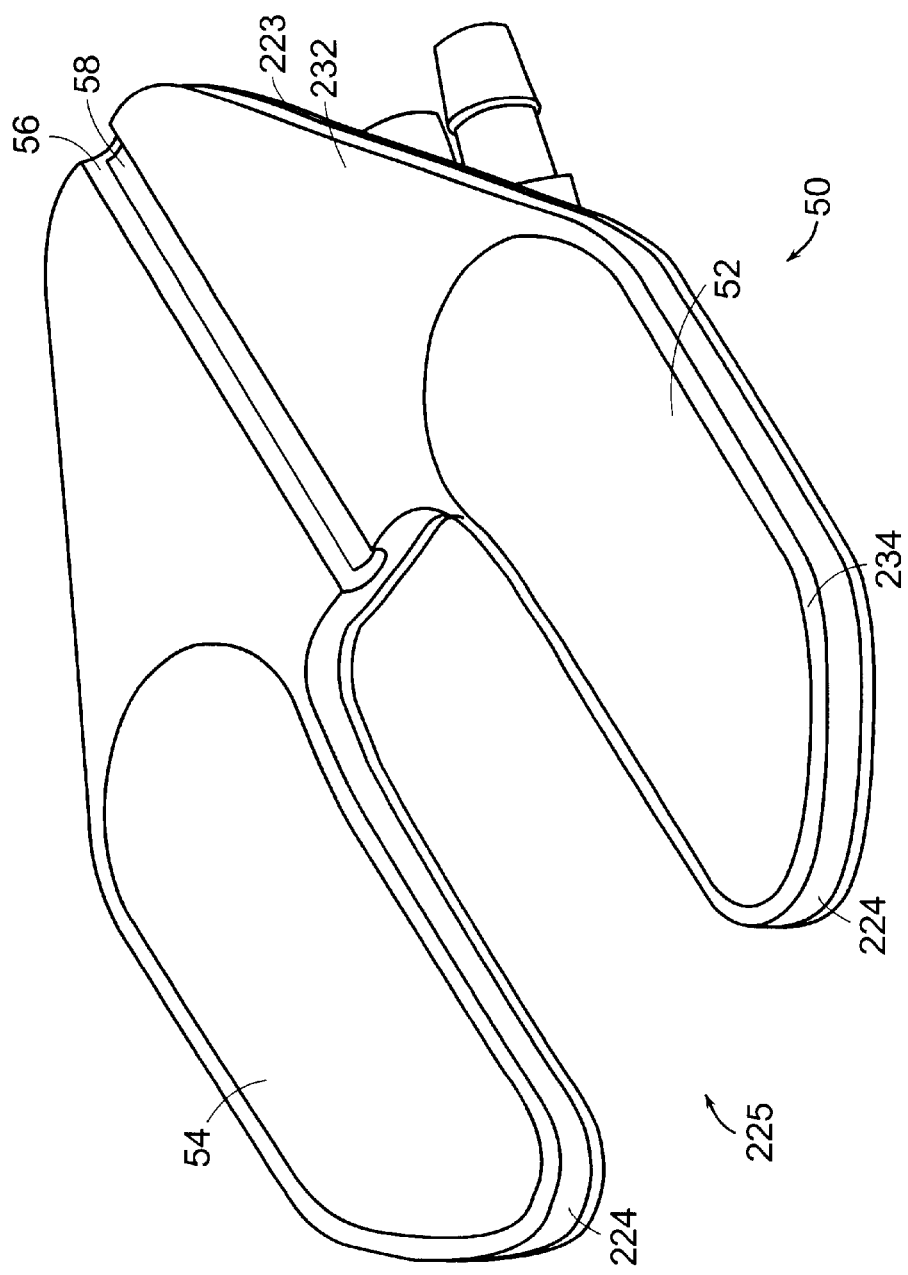
FIG. 8 is a perspective view of a third example of a cooled stabilizer with a depressed portion on the heel.

A further example of a cooled stabilizer 50 according to the present invention is depicted in FIG. 8, in which like reference numerals are duplicated and preceded by a "2". The stabilizer includes a heel 223 and horseshoe sections 224, with respective bottom surfaces 232 and 234. The bottom surface 234 is covered almost entirely by pads 52 and 54, for providing a substantially even distribution of cooling over the horseshoe sections. The channels (not shown) are attached underneath the pads in any suitable configuration, e.g., around the periphery of the pads or in a center region thereof. By providing large pads made of thermally conductive material covering the bottom surface 234, the surface can be maintained at a substantially uniform temperature, thereby providing a uniform chilled surface for cooling body tissue over a relatively large surface area of the tissue.

As shown in FIG. 8, the bottom surface 232 in the heel is generally insulated, but is further provided with a groove 56 bored into the bottom surface 232 and running in approximately a straight line distally through a central portion of the heel 223 and toward the central opening 225. A lower surface of the groove 56 can include a thermally conductive pad 58 for providing cooling over a surface thereof. The groove 56 can function as a relief, allowing the coronary artery to lay within the groove, thus cooling tissue adjacent to the coronary artery for inducing hemostasis.

Figure 9:
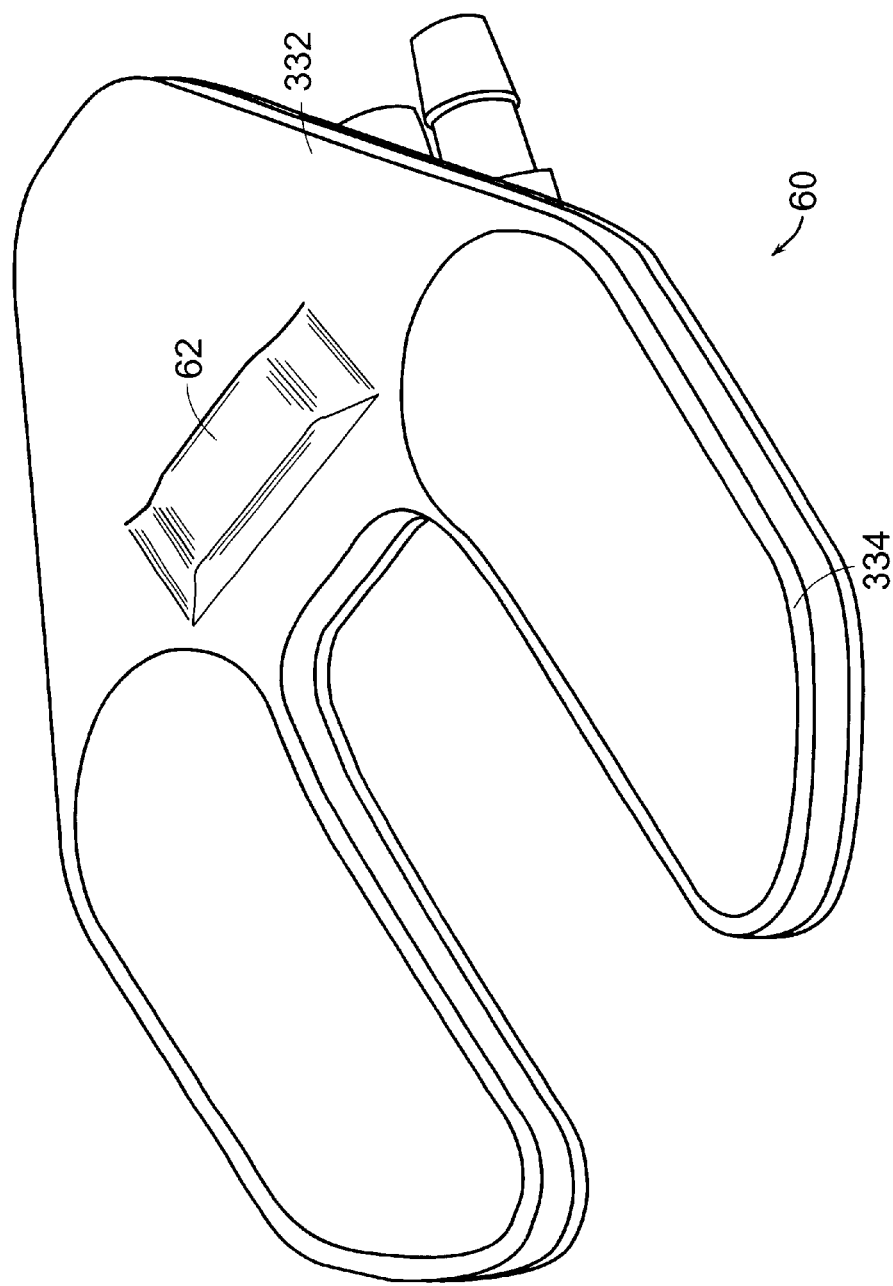
FIG. 9 is a perspective view of a fourth example of a cooled stabilizer with a raised portion on the heel.

FIG. 9 illustrates a further example of a cooled stabilizer 60 according to the present invention. In FIG. 9, a bottom surface 334 in the horseshoe sections is configured in a manner similar to the horseshoe sections in FIG. 8, and accordingly further description thereof is omitted. A bottom surface 332 of the heel is provided as an insulated surface, and includes a raised downwardly extending portion 62 for providing compression of the artery in the vicinity of the heel. The raised portion 62 can be formed as a plateau with tapered sides, or in any other suitable configuration such as a box-like shape. The bottom surface 332 is generally flat, except for any desired texture on the raised portion, which can be used to provide additional compression on the coronary artery.

Figure 10:
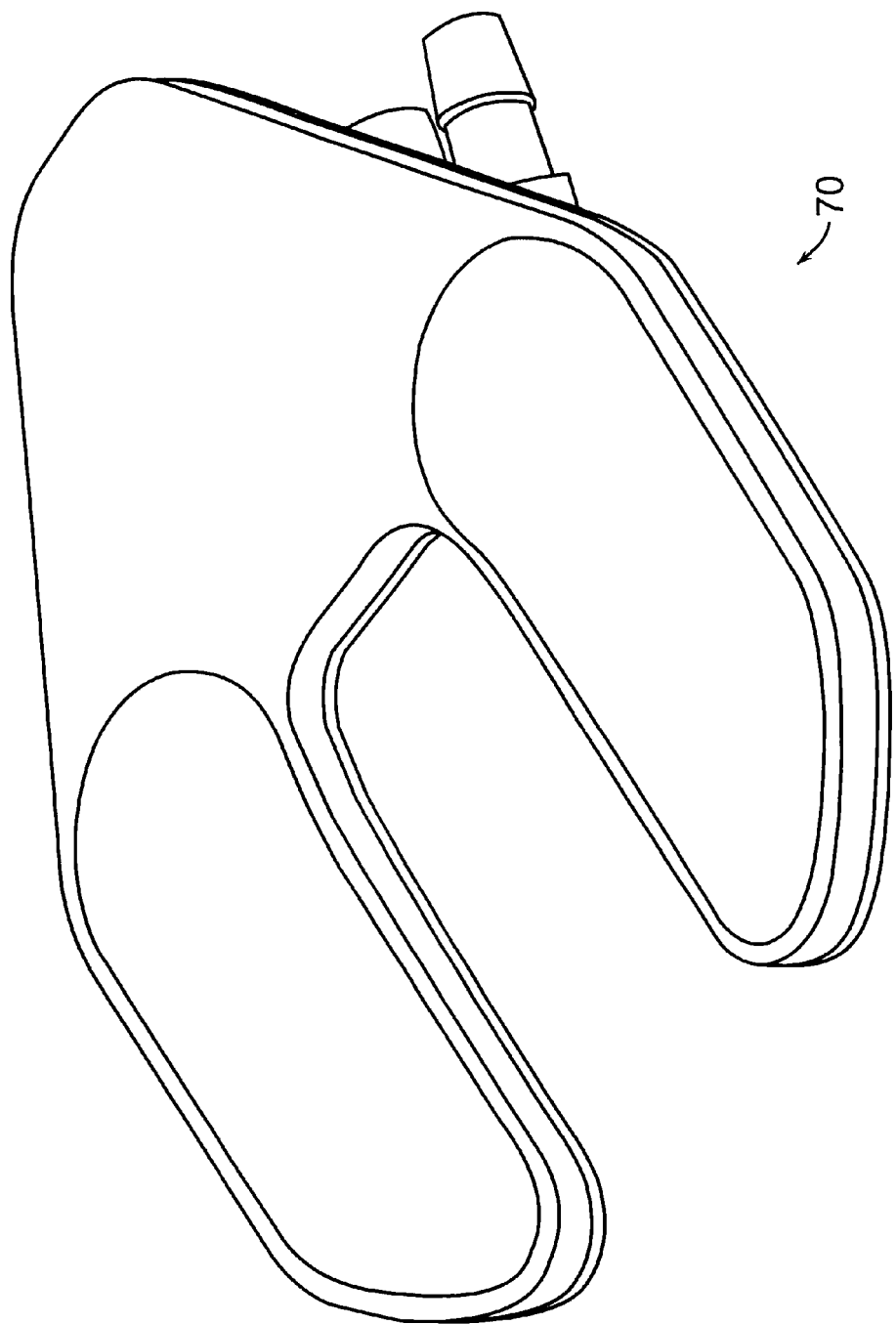
FIG. 10 is a perspective view of a fifth example of a cooled stabilizer.
Figure 11:
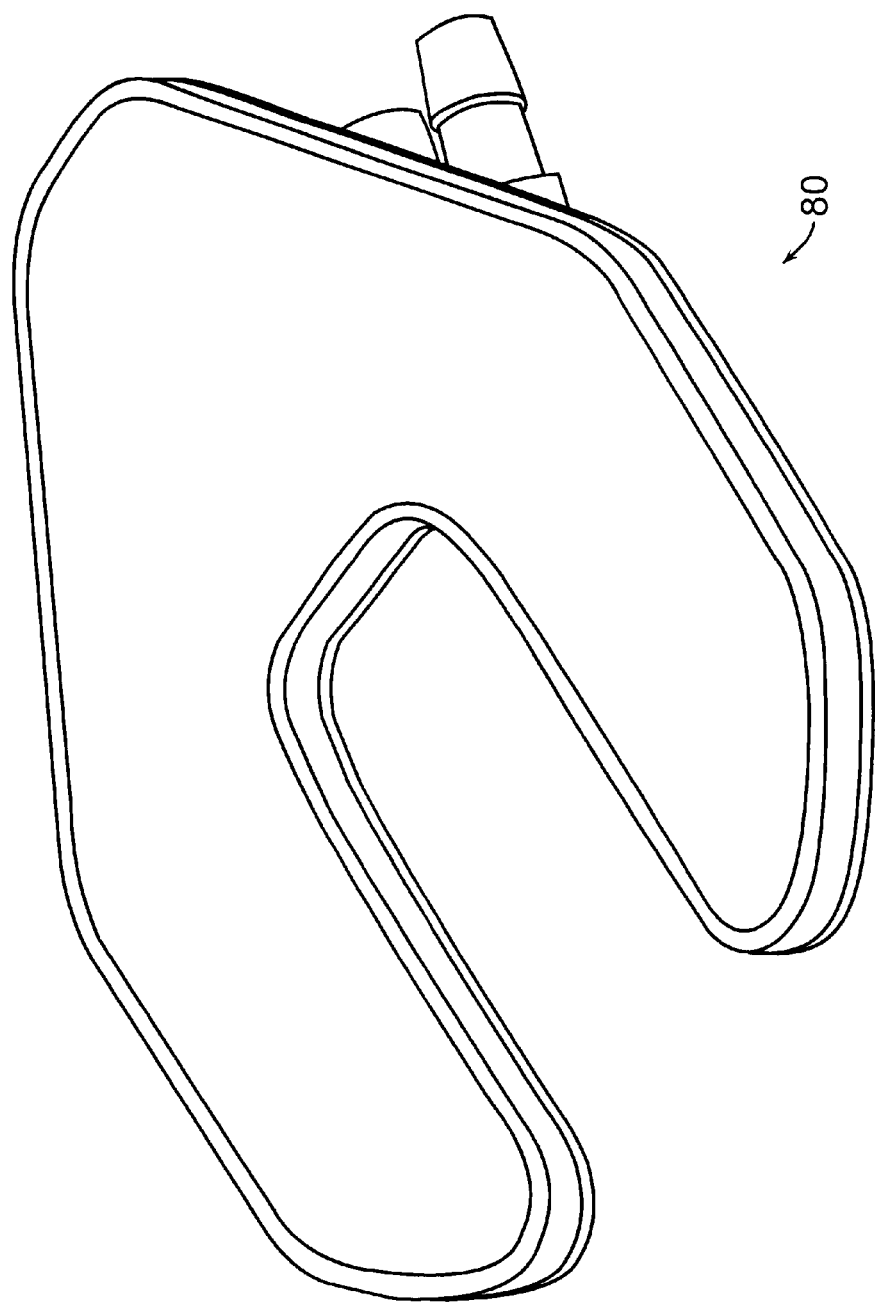
FIG. 11 is a perspective view of a sixth example of a cooled stabilizer.

FIGS. 10 and 11 illustrates further examples of a cooled stabilizer which are variations of the previously cited examples. For example, FIG. 10 illustrates a cooled stabilizer 70 in which a bottom surface of the horseshoe sections includes pads covering substantially the entire bottom surface thereof for the transfer of the cooling effect of the coolant therefore, and thus is similar to the arrangements depicted in FIGS. 8 and 9. In FIG. 10, a substantially flat insulating surface covers the channels in the heel, thereby preventing a chilled surface from contacting body tissue in the heel.

In FIG. 11, one or more thermally conductive pads cover the entire bottom surface of the cooled stabilizer 80, so that a chilled surface is provided over the entire bottom surface of the stabilizer.

Figure 12:
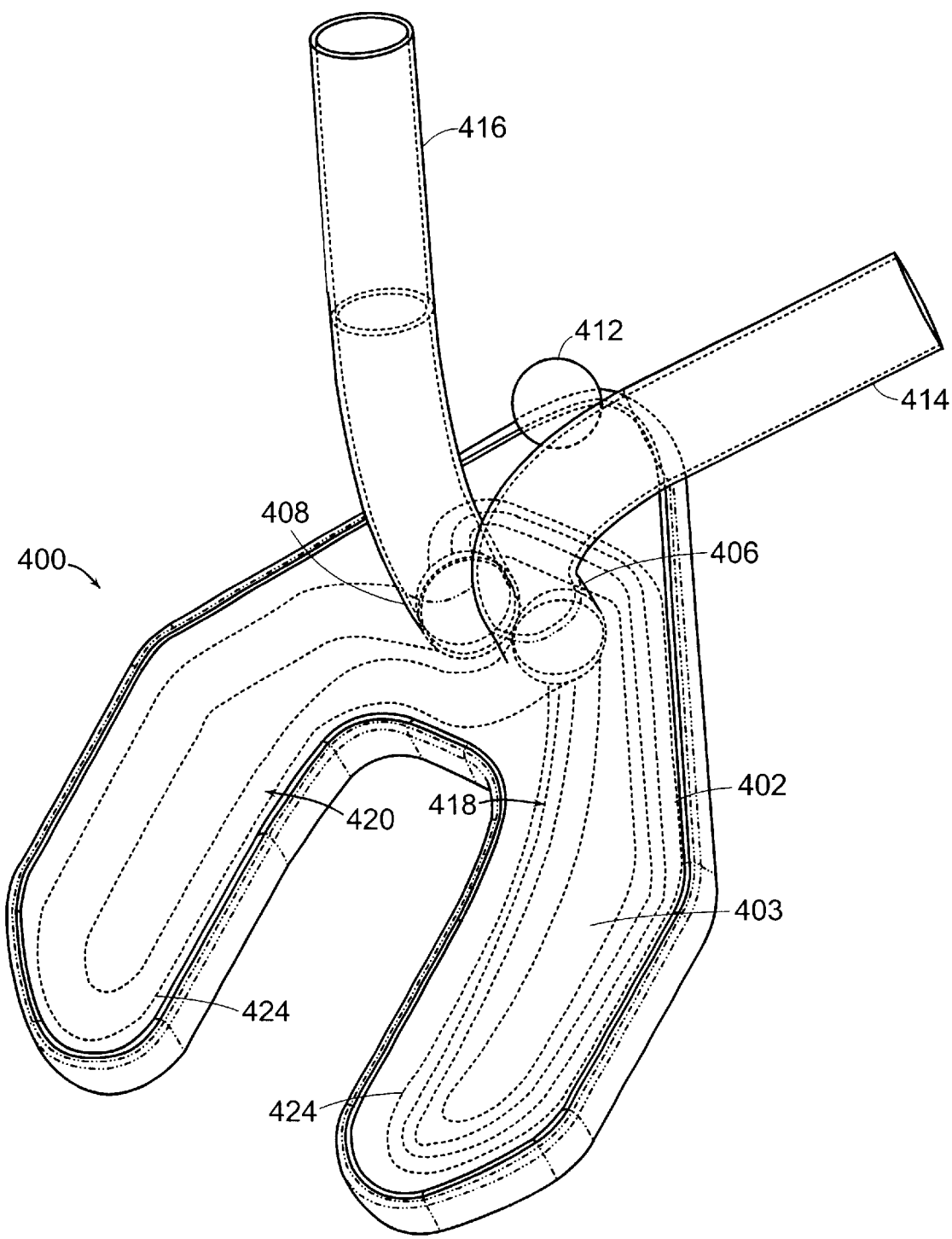
FIG. 12 is a perspective view of a seventh example of a cooled stabilizer showing channels inside the stabilizer.
Figure 13:
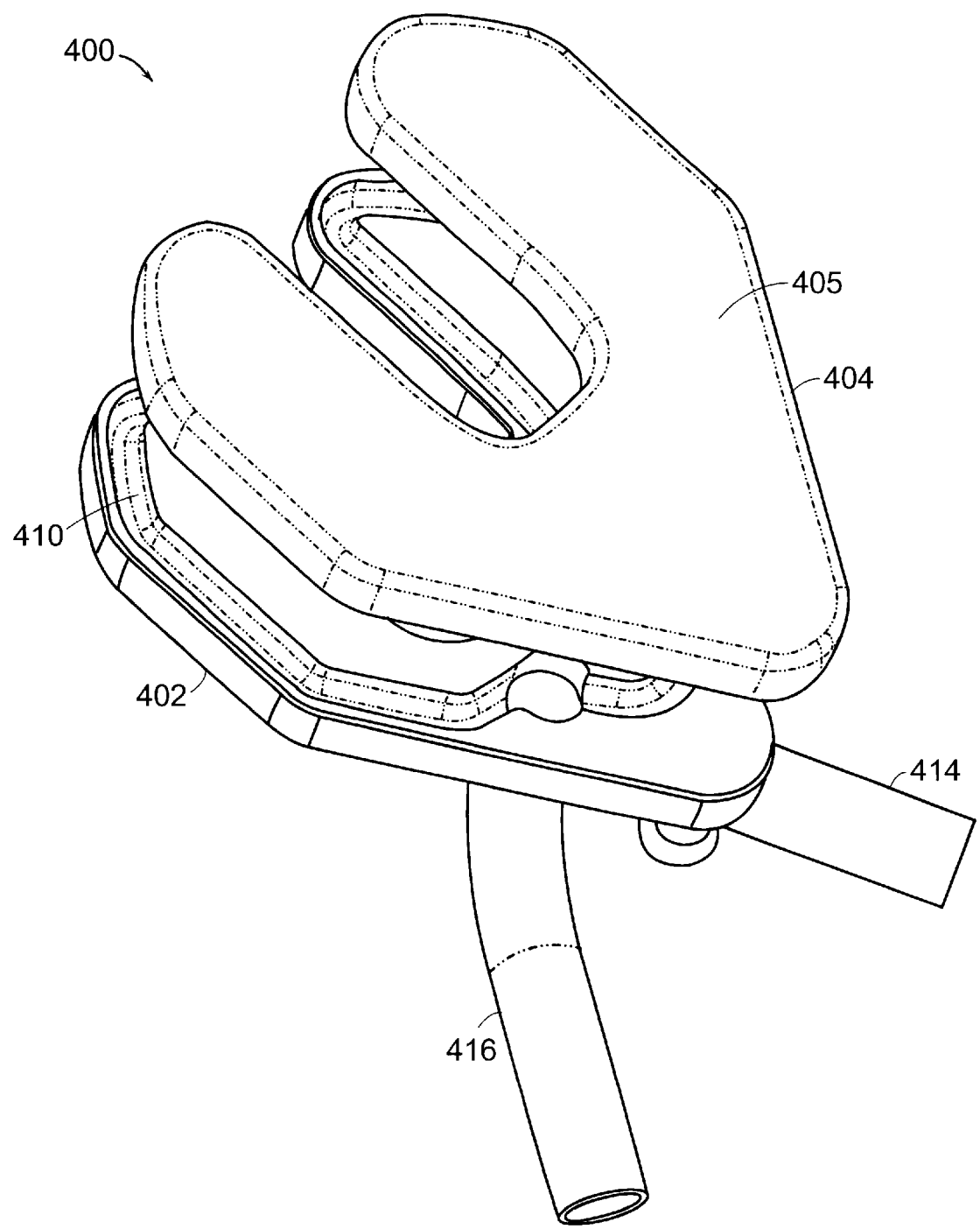
FIG. 13 is an exploded perspective view of the cooled stabilizer shown in FIG. 12.

FIGS. 12 and 13 illustrate an example of a cooled stabilizer 400 in which a pair of complimentary plates 402, 404 are telescoped together, with a continuous channel running through the combined plates for circulating fluid. First and second plates 402 and 404, respectively, are complimentary and include opposed inner surfaces, each having respective portions of a channel 410 formed therein. When the plates are joined, the channel portions combine to form the continuous channel 410 for circulating fluid through the stabilizer.

As shown in FIG. 12, the first plate can include a substantially flat, continuous outer surface (i.e., upper surface) 403 having openings serving as an inlet 406 and an outlet 408, which are connected to lines 414 and 416, respectively. The inlet and outlet can be reversed in orientation, or each can receive a plurality of lines. The lines are connected to an outside cooling source (not shown) and serve to transport fluid toward and/or away from the stabilizer, so that a fluid such as cooling fluid can be circulated in the stabilizer. The outer surface 403 of the first plate 402 can be an insulated surface to avoid histological side effects at the graft site, or alternatively can be a thermally conductive surface to provide additional chilling effect. In certain embodiments, the outer surface 403 can have both insulating and conductive portions. The first plate 402 further includes a joint 412, e.g., as part of a ball-and-socket joint, for connecting with an elongated arm or other instrument (not shown).

As shown in FIG. 13, the second plate 404 includes a substantially flat, continuous, thermally conductive outer surface (i.e., bottom surface) 405 which can provide a chilled surface in contact with body tissue at a targeted area of the graft site. Optionally, portions of the outer surface 405 can be insulating. In FIG. 13, cut-out sections which form the channel 410 are visible in the first plate 402. The combined channel produced when the first and second plates are joined together is shown in outline form in FIG. 12. The channel 410 can include a single continuous channel or a plurality of channels running along the surfaces adjacent to and spaced apart from the area between the arms of the horseshoe. The channels of this embodiment preferably are milled into the plates 402 and 404. Plates 402 and 404 also can be made by press fitting, stamping, or other conventional manufacturing processes.

FIG. 12 illustrates one possible arrangement of paths defined by the continuous channel within the stabilizer. For example, after the inlet 406 the channel can be subdivided into first and second paths 418 and 420, respectively, for circulating fluid to elongate members (e.g. horseshoe sections 424) of the stabilizer. By subdividing fluid at the inlet, the two sections 424 can be maintained at approximately the same temperature or within a closer range of temperatures as compared to an arrangement providing a single path between the inlet and outlet. The two paths 418 and 420 can rejoin at the outlet 408.

In one embodiment of the stabilizer shown in FIGS. 12 and 13, the inner and outer surfaces of both plates are made of a thermally conductive material, and therefore the entire inner and outer surfaces function as a heat exchanger capable of circulating cooling fluid and removing heat from the targeted area, thereby providing traction and quiescence to the targeted tissue, while also potentially being capable of inducing hemostasis in adjacent body tissue.

In another possible embodiment of the stabilizer of FIGS. 12 and 13, the outer surface 403 of the first plate 402 can be an insulating surface, and the outer surface 405 of the second plate can include thermally conductive material over at least a portion of the surface. The outer surface 405 further can include one or more pads having a surface thereon for providing traction, as discussed above in conjunction with other examples of the present invention.

Figure 14:
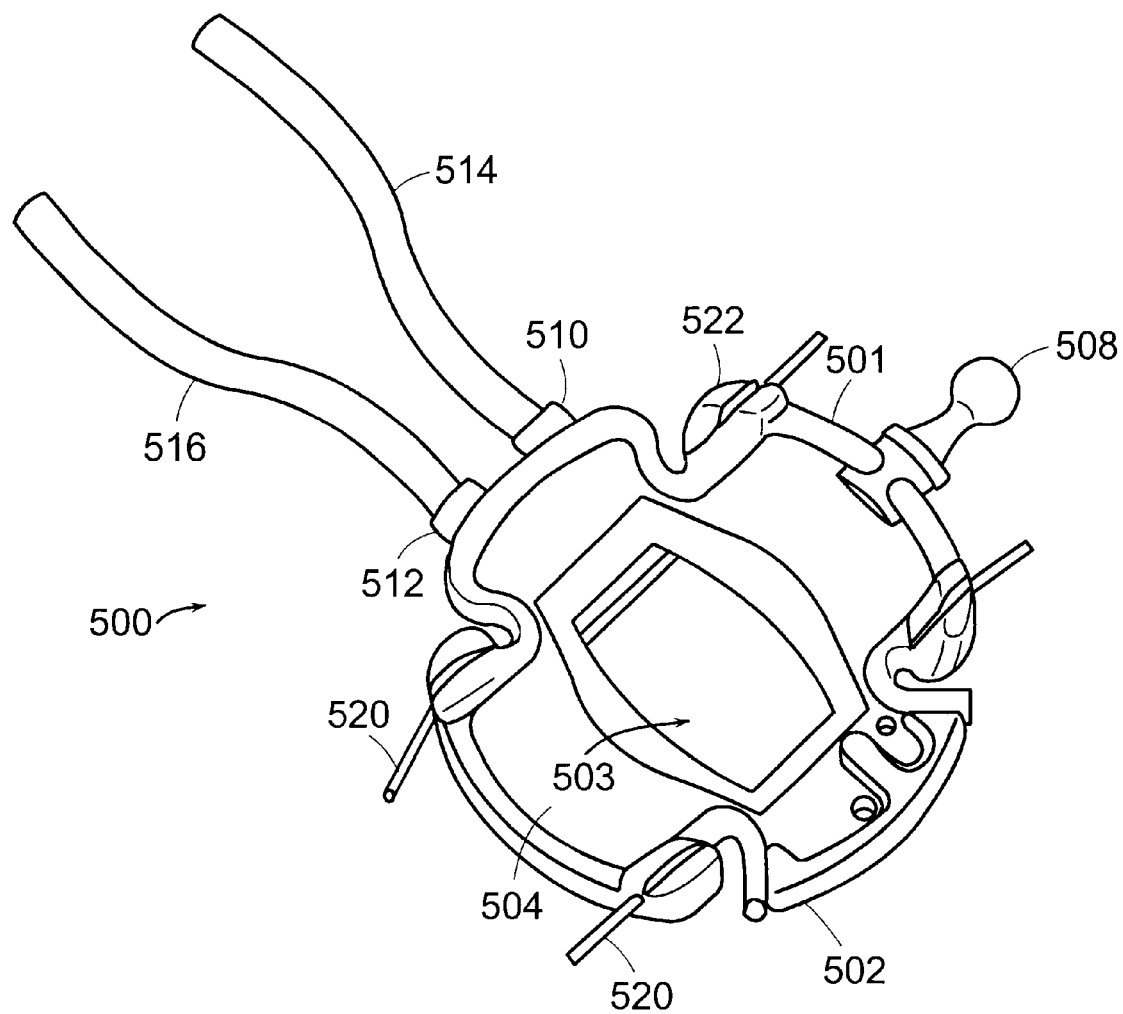
FIG. 14 is a top perspective view of an eighth example of a cooled stabilizer.

FIGS. 14–17 illustrate an example of a cooled stabilizer 500 further incorporating the use of flexible tapes and a removable end piece 502. The cooled stabilizer of this embodiment includes a member 501 having a generally closed horseshoe shape defining a central opening 503 which is closed by the heel, arms, and end piece 502. The member 501 can comprise one or more plates having an upper surface 504 and a bottom surface 506, the bottom surface for contact with body tissue such as the epicardium. Channels 514 and 516 are connected to an inlet 510 and an outlet 512, respectively, and can distribute fluid via channels (not shown) in the member 501. The member 501 can include a joint 508 such as the ball of a ball and socket connector mounted on the outer surface of the member 501 for attaching the cooled stabilizer to an elongated arm or other instrument (not shown). As shown in FIG. 14, the joint 508 preferably is positioned along a side of the member 508 parallel to the bottom surface 506 of the member 501. The joint also can be arranged in another orientation or in a different plane from the bottom surface 506 of the member 501.

The bottom surface 506 of the member 501 can be a thermally conductive surface for presenting a chilled surface in contact with body tissue when a cooling fluid is circulated through the cooling channels/conduits. The bottom surface 506 further can be provided with one or more thermally conductive pads 518 which can include a textured surface to provide additional traction in a targeted area adjacent a graft. The upper surface 504 can be provided as an insulated or, alternatively, a thermally conductive surface as desired.

Figure 15:
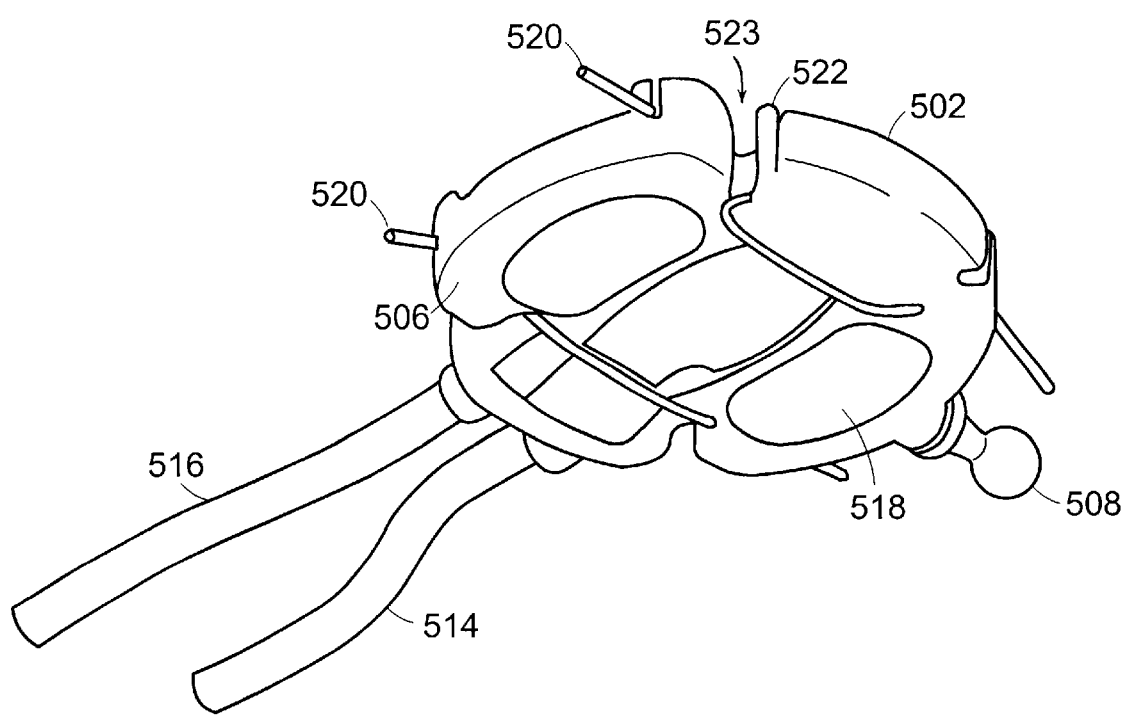
FIG. 15 is a bottom perspective view of the cooled stabilizer of FIG. 14.

As shown in FIGS. 14 and 15, one or more and preferably two flexible tapes 520 can be threaded through body tissue in the targeted area to provide temporary vessel occlusion. Once the stabilizer is positioned in the desired orientation and location in contact with the body tissue, the flexible tapes 520 are pulled snug through an opening 523 formed in a slotted section 522 of the stabilizer. The stabilizer can include a plurality of openings 523 and corresponding slotted sections 522, depending on the number of flexible tapes 520 attached to the stabilizer. Suitable flexible tapes include silastic tapes or similar known materials.

Figure 16:
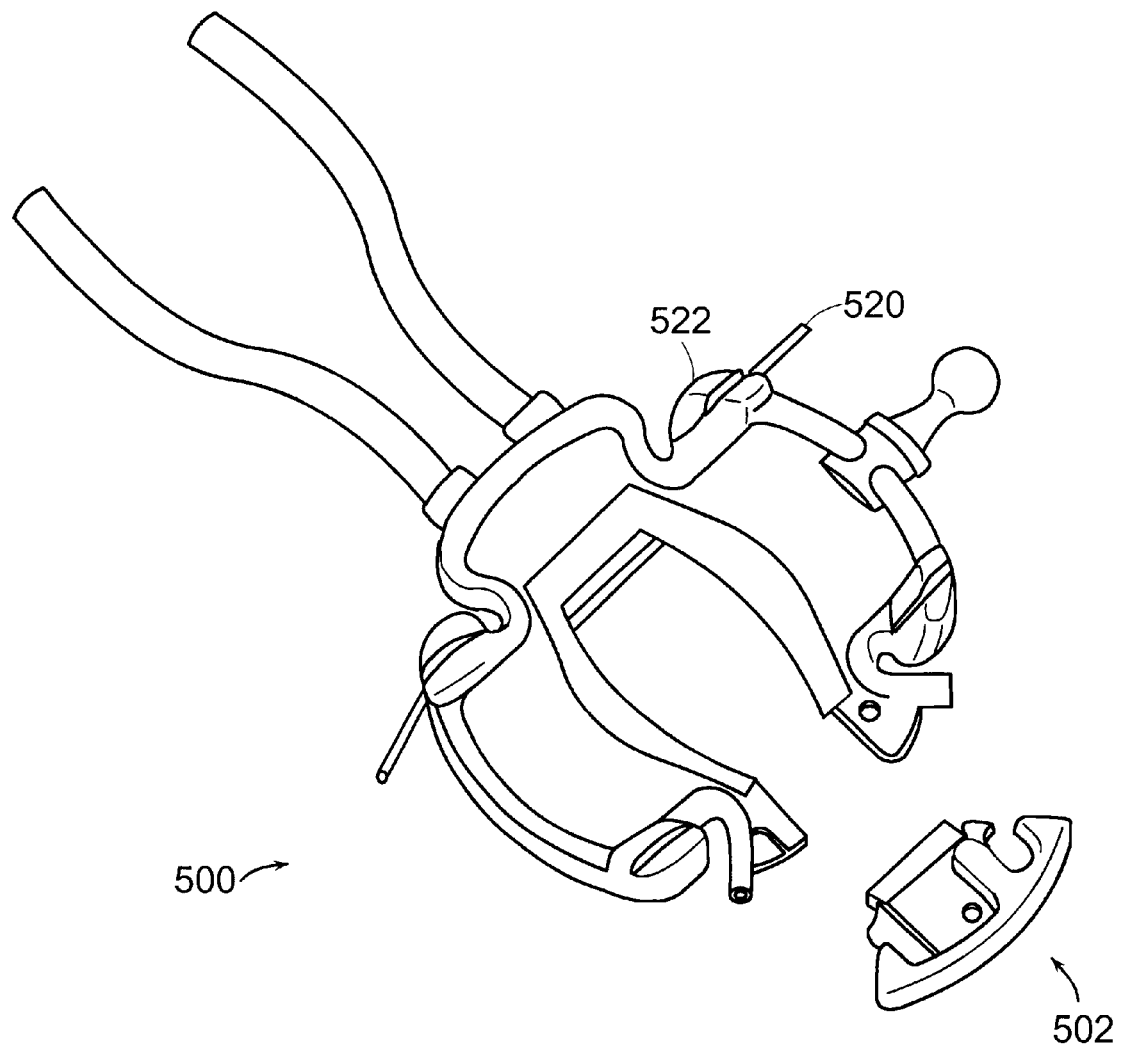
FIG. 16 is a top perspective view of the cooled stabilizer of FIG. 14 after an end piece has been removed.
Figure 17:
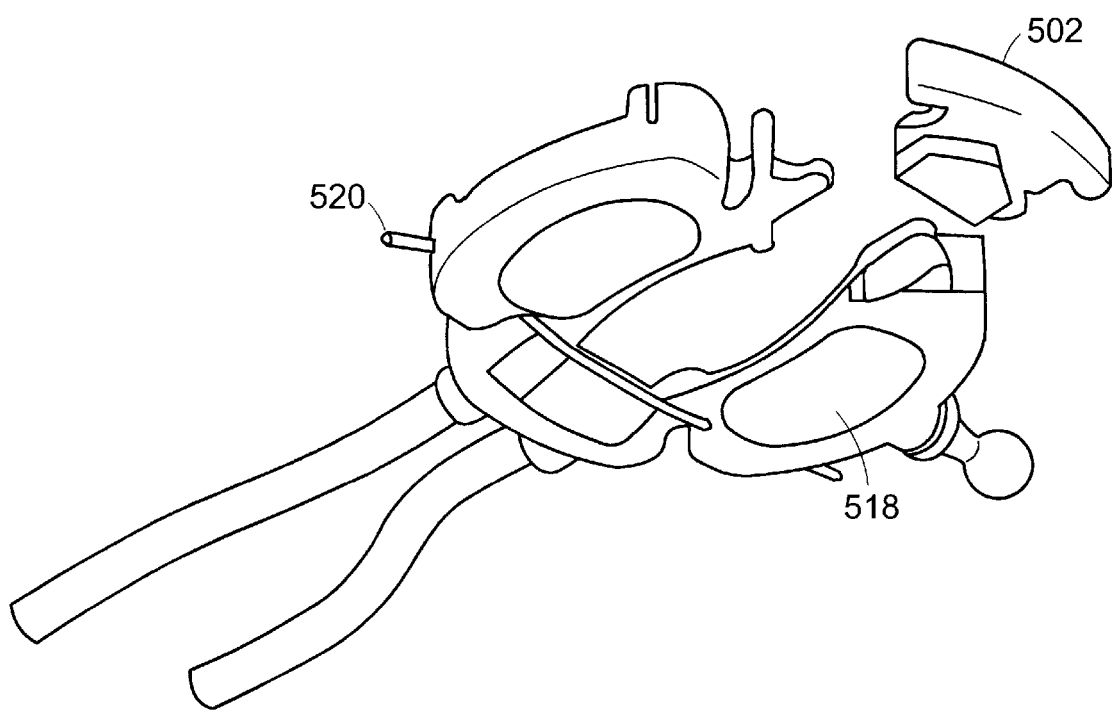
FIG. 17 is a bottom perspective view of the cooled stabilizer of FIG. 16, i.e., after the end piece has been removed.

As shown in FIGS. 16 and 17, after a surgical procedure (e.g., an anastomosis) is completed, the end piece 502 can be removed from the member 501 to facilitate removal of member 501 from around the graft. The tapes 520 (see FIG. 14) can be easily removed, thereby permitting easy removal of the member 501 and access into the central opening 503.

Figure 18:
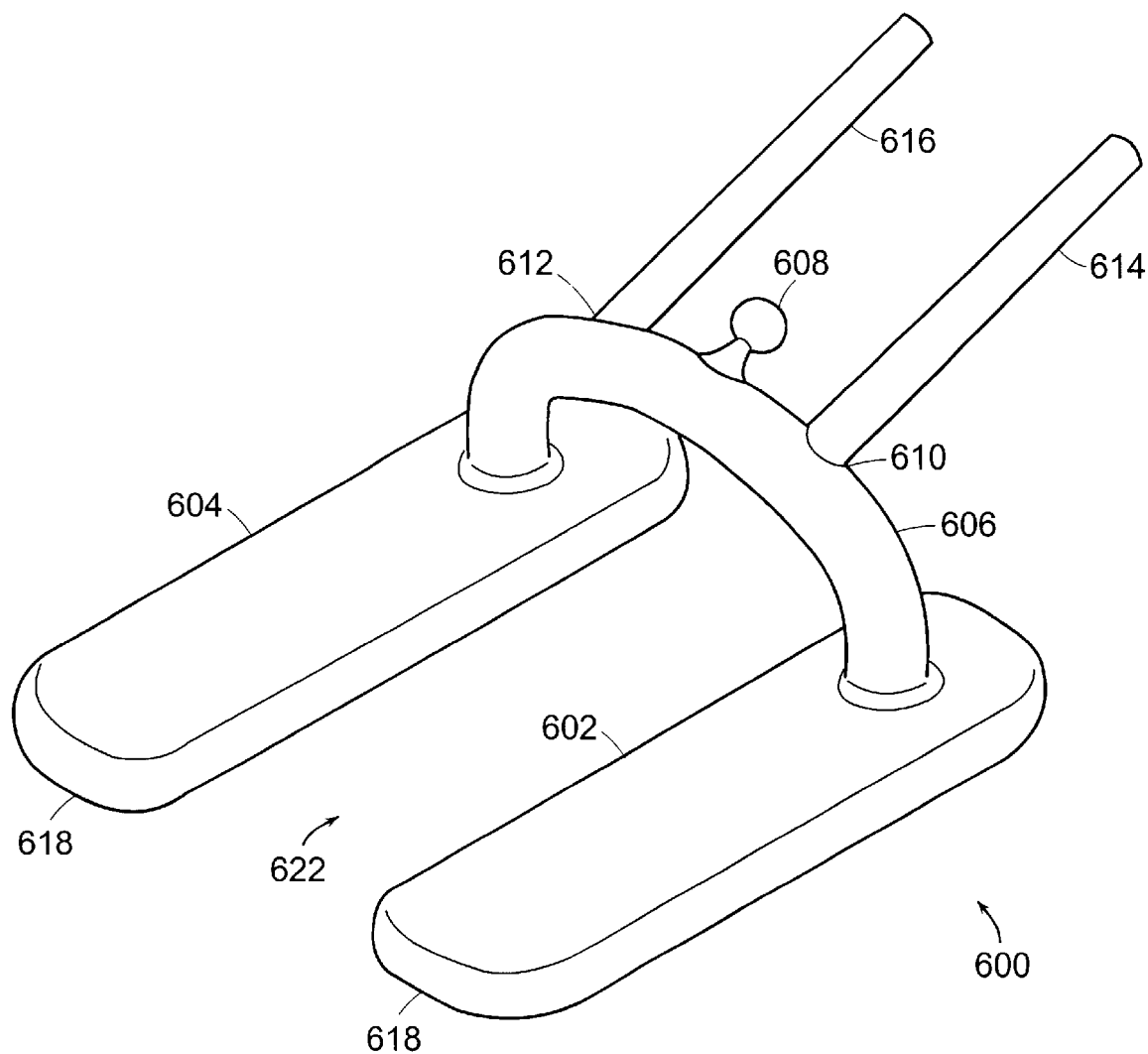
FIG. 18 is a top perspective view of a ninth example of a cooled stabilizer.
Figure 19:
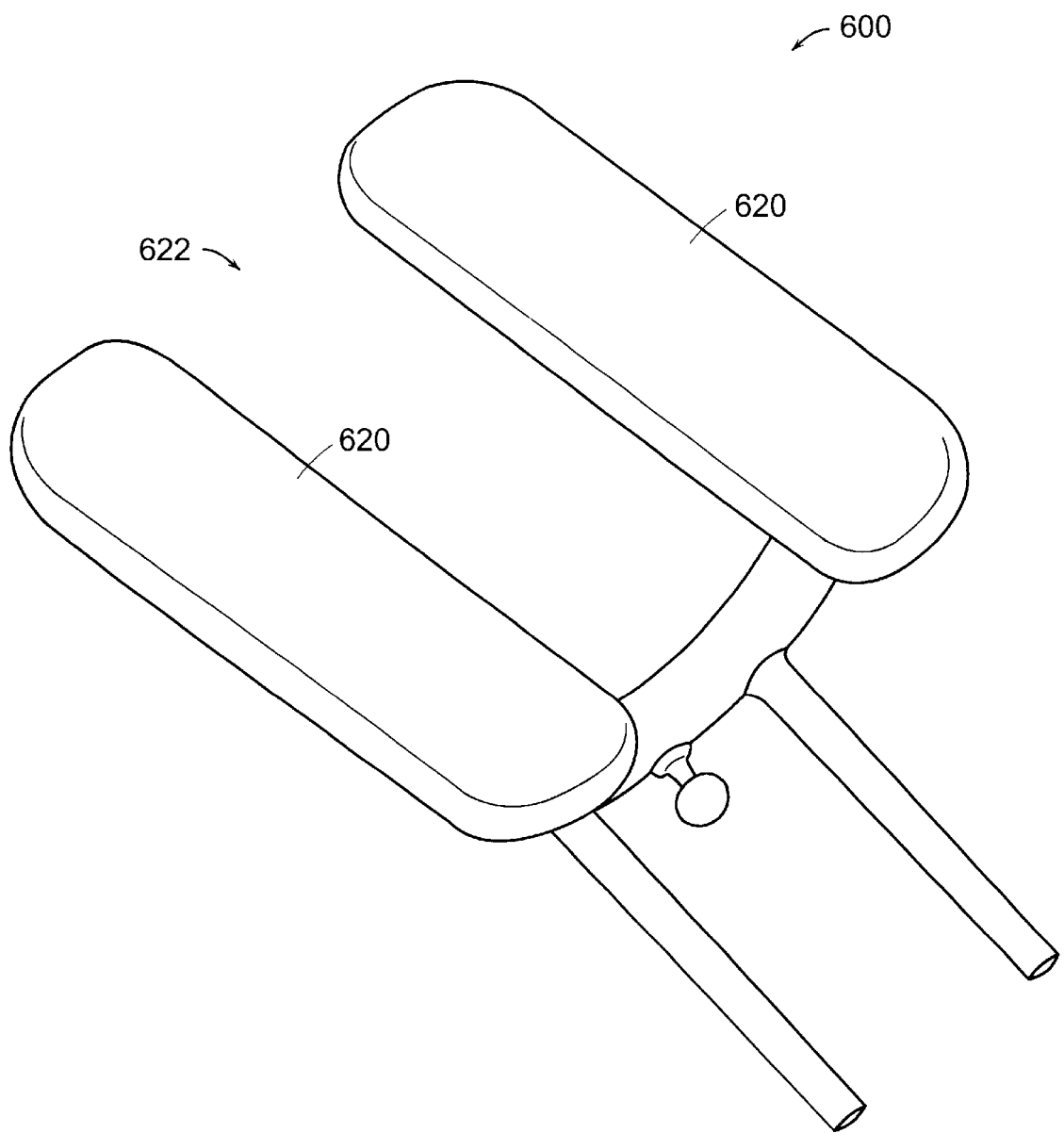
FIG. 19 is a bottom perspective view of the cooled stabilizer of FIG. 18.

FIGS. 18 and 19 illustrate an example of a cooled stabilizer 600 having at least two members 602, 604 preferably arranged approximately parallel to each other, thereby defining a central opening 622 therebetween (i.e., a window) for performing a surgical operation. Each member 602, 604 can be formed from one or more plates having upper surfaces 618 and bottom surfaces 620. The bottom surfaces 620 preferably are made from a thermally conductive material, while the upper surfaces 618 can be either thermally conductive or insulative.

A raised or generally U-shaped connecting member 606 can be attached to the members 602, 604, preferably at a proximal end thereof, although the connecting member 606 can be arranged at any position along the members 602, 604. The member 606 can include a joint 608 such as the ball of a ball and socket connector mounted on the outer surface of the member 606 for attaching the cooled stabilizer to an elongated arm or other instrument (not shown). As shown in FIGS. 18 and 19, the connecting member 606 is a generally semicircular, arc-like plate or tube containing one or more channels or conduits for transmitting fluid. Fluid is delivered to and expelled fro the connecting member 606 via an inlet 610 and an outlet 612, respectively, although the orientation of the inlet and outlet can be reversed. Preferably, the inlet 610 is connected to one or more channels or conduits 614, and the outlet 612 is connected to one or more channels or conduits 616. Additionally, one or more channels or channels (not shown) can be provided to circulate fluid through the connecting member 606 and members 602, 604. For example, the inlet 610 can receive a channel 614 which is subdivided in to a plurality of channels or conduits for forming separate closed loops in each member 602, 604. Other arrangements can be provided such as multiple closed loops through each member 602, 604.

An exemplary method of using a cooled stabilizer according to the present invention will now be discussed. In use, the cooled stabilizer of the present invention, e.g., with reference to the example shown in FIGS. 12 and 13, can be attached to a flexible or rigid arm, which can be positioned along a rail of a retractor.

One end of each channel 414 and 416 can be connected to the inlet 406 and outlet 408, respectively, of the cooled stabilizer 400. Opposite ends of the channels can be connected to an open loop or closed loop system (not shown) for distributing fluid to the cooled stabilizer. The circulating fluid can be a cooling fluid, as discussed above, and a conventional medically acceptable refrigeration system (not shown) can be used to chill the fluid to the desired temperature. Examples of suitable refrigeration systems include chillers, conventional hospital refrigeration units, and/or ice baths. Preferably the fluid being circulated is a saline solution, an alcohol solution, or a saline/alcohol solution, and more preferably a saline solution. A standard, conventional pump (not shown) can be provided to pump the fluid through channels 414, 416 and through the channel 410 in the stabilizer.

Once fluid is being circulated through the cooled stabilizer, the arm and stabilizer can be attached to the retractor, which is inserted into the chest of a patient in a known manner. The exact sequence of steps such as arranging the arm and stabilizer on the retractor, placing the retractor on the patient's chest, and beginning to circulate fluid through the stabilizer is not critical; however, it is preferred to have the fluid circulated through the stabilizer before the stabilizer is placed at the graft site. The targeted area is then preferably dried to provide a clear contact surface. The arm and stabilizer are positioned in a desired orientation in order to contact the targeted area of the epicardium, i.e., over a coronary artery grafting site. Preferably the heel of the stabilizer is placed over the coronary artery in a known manner such that the horseshoe sections surround or are aligned adjacent to the coronary artery, and the grafting site is accessible through the opening.

When traction and quiescence of the targeted tissue are achieved over a targeted area adjacent the graft site, the surgeon proceeds with the graft and performs an anastomosis or other surgical operation. Appropriate placement of the cooled stabilizer can induce hemostasis in the targeted area. Optionally, one or more flexible tapes can be attached to the cooled stabilizer in a known manner to provide both compression and lifting forces on the epicardium, which can further assist in inducing hemostasis.

After completion of the CABG procedure, e.g., with reference to FIGS. 12 and 13, the pump can be slowed or stopped to reduce the flow rate of fluid circulating through the channel 410. Alternatively or additionally, fluid having a warmer temperature than the cooling fluid can be circulated through the stabilizer. By reducing the flow rate or increasing the temperature of the fluid, the bottom surface 405 becomes warmed, and the stabilizer can more easily be released from the graft site.

In accordance with the present invention, the cooled stabilizer can provide suitable compression as in existing stabilizers, but also can induce tissue quiescence in a localized area where the chilled surface contacts the epicardium and/or the coronary artery. By inducing tissue stability, quiescence and/or hemostasis in the targeted area, a substantially bloodless field can be provided for performing surgical operations. Tissue stability and/or quiescence preferably is induced wherever the chilled surface of the stabilizer is in contact with the epicardium, at least in the horseshoe sections of the stabilizer. The chilled surface also can be provided in the heel of the stabilizer, unless an insulating surface covers the heel.

The stabilizer of the present invention preferably provides traction and quiescence over a targeted area adjacent a graft site and can be capable of inducing hemostasis in the heart or another organ of the body. While the above description provides details with respect to a horseshoe-shaped stabilizer and a stabilizer having parallel members, other shapes can be used, so long as at least one element of the stabilizer receives fluid through one or more channels and includes a bottom surface, a portion of which can be thermally conductive to transfer the effect of a fluid having a temperature less than the normal tissue temperature in contact with body tissue and/or an artery. To maximize surface area of the thermally conductive surface, the channels can be positioned along a periphery of the member, can be covered by one or more pads, or can be replaced by channels within one or more plates forming the member(s).

Although exemplary embodiments of the invention have been described using specific terms, such description is for illustrative purposes only, and it is to be understood that changes and variations may be made without departing from the spirit or scope of the following claims. One possible modification is to circulate warmed fluid through the stabilizer instead of cooling fluid, and to therefore heat a targeted area of body tissue and/or an artery periodically during or following the procedure. As discussed herein, higher temperature "cooling" fluids can be circulated after completion of a CABG procedure, in order to release the cooled stabilizer from contact with the graft area. Further modifications to the stabilizer include providing malleable members (or horseshoe sections), such that the stabilizer can be bent to accommodate a given targeted area of the graft site.

What is claimed is:

1. A stabilizer for use in surgical procedures, comprising:
   a first member having an upper surface and a bottom surface;
   a second member having an upper surface and a bottom surface;
   a further interconnecting member interconnecting the first member and the second member, wherein the first member, second member and interconnecting member are in a horseshoe shape and wherein the interconnecting member includes a bottom surface that forms a continuous plane with the bottom surface of the first member;
   a channel for circulating fluid through the first and second member; and
   a surface portion made of thermally conductive material positioned on the bottom surface generally adjacent to the channel, the surface portion contacting body tissue and reducing the temperature thereof.

2. The stabilizer of claim 1, wherein the interconnecting member further includes a joint for pivotally attaching the stabilizer to an arm.

3. The stabilizer of claim 1, wherein the first member and the second member are positioned around a grafting site and are formed to reduce the temperature thereof, and the interconnecting member contacts an artery.

4. The stabilizer of claim 1, wherein the bottom surface of the interconnecting member is an insulated surface.

5. The stabilizer of claim 4, wherein the insulated bottom surface of the interconnecting member includes a downwardly extending portion that is aligned generally perpendicular to a lengthwise dimension of the first member.

6. The stabilizer of claim 1, wherein the bottom surface of the interconnecting member includes an insulated surface and a groove running through the insulated surface.

7. The stabilizer of claim 6, and further including a thermally conductive surface portion positioned in the groove.

8. The stabilizer of claim 1, wherein the surface portion covers a portion of the bottom surface of the first member.

9. The stabilizer of claim 1, wherein the surface portion covers substantially the entire bottom surface of the first member.

10. The stabilizer of claim 1, and further including an elongate opening in the first member for receiving a flexible tape.

11. A stabilizer for use in surgical procedures, comprising:
    a first member having an insulated upper surface and a thermally conductive bottom surface; a second member having an insulated upper surface and a thermally conductive bottom surface;
    a further interconnecting member interconnecting the first member and the second member, wherein the first member, second member and interconnecting member are in a horseshoe shape and wherein the interconnecting member includes a bottom surface that forms a continuous plane with the bottom surface of the first member; and
    a cooling channel formed generally adjacent to the bottom surface of the first and second member around a periphery thereof for circulating cooling fluid through the member, the cooling channel being made of a thermally conductive material.

12. The stabilizer of claim 11, wherein the first member and the second member are sized to be positioned generally adjacent to a grafting site, and the interconnecting member contacts tissue adjacent to an artery.

13. A system for stabilizing and cooling a predetermined area of body tissue during surgical procedures, comprising:
    an elongated arm connected to a surgical retractor; and
    a stabilizer attached to a distal end of the elongated arm, the stabilizer comprising:
      a first member having an insulated upper surface and a thermally conductive bottom surface;
      a second member having an insulated upper surface and a thermally conductive bottom surface;
      a further interconnecting member interconnecting the first member and the second member, wherein the first member, second member and interconnecting member are in a horseshoe shape and wherein the interconnecting member includes a bottom surface that forms a continuous plane with the bottom surface of the first member;
      a cooling channel for circulating cooling fluid through the first and second member; and
      a surface portion of the first and or the second member made of thermally conductive material positioned generally along the bottom surface and adjacent to the cooling channel, the surface portion for contacting and reducing the temperature of the body tissue.

14. The stabilizer of claim 13, wherein the first member and the second member include inner portions adjacent to each other and outer portions spaced apart from each other and are sized to be positioned adjacent to a grafting site.

15. The system of claim 14, wherein the inner portions of the first member and the second member include cooling fluid circulated through a cooling channel associated therewith.

16. The system of claim 14, wherein the outer portions of the first member and the second member include cooling fluid circulated through a cooling channel associated therewith.

17. The system of claim 14, wherein the inner portions and outer portions of the first member and the second member include cooling fluid circulated through a cooling channel associated therewith.

18. The system of claim 15, wherein the bottom surface of the interconnecting member includes an insulated surface and a groove running through the insulated surface.

19. The system of claim 18, and further including a thermally conductive surface portion positioned in the groove.

20. The stabilizer of claim 13, wherein the surface portion substantially covers the bottom surface of the first member.

21. The stabilizer of claim 13, wherein the surface portion covers an elongate portion of the bottom surface of the first member.

22. A stabilizer for use in surgical procedures, comprising:
a first section having inner and outer surfaces, the outer surface receiving one or more lines that are connected to a channel portion formed in the inner surface; and
a second section having a thermally conductive outer surface and an inner surface including a channel portion formed in the inner surface, wherein the first and second sections are interconnected together such that the channel portion of the first section combines with the channel portion of the second section to form a continuous channel for circulating fluid through the stabilizer and further including a surface portion made of thermally conductive material positioned on the outer surface of the second section.

23. The stabilizer of claim 22, wherein the outer surface of the first section is made of thermally conductive material.

24. The stabilizer of claim 22, wherein the outer surface of the first section is made of insulating material.

25. The stabilizer of claim 22, wherein the one or more lines received on the first section comprise first and second lines, the first line connected to an inlet on the first section, and the second line connected to an outlet on the first section.

26. The stabilizer of claim 25, wherein the continuous channel forms a plurality of paths through the stabilizer.

27. The stabilizer of claim 26, wherein the continuous channel connected to the inlet subdivides into first and second paths, thereby forming two paths for circulating fluid in the stabilizer.

28. The stabilizer of claim 26, wherein the first and second paths are joined together at the outlet.

29. A stabilizer for use in surgical procedures, comprising:
first and second members, each having an upper surface and a thermally conductive bottom surface;
a connecting member for connecting the first and second members wherein the first member, second member and connecting member are in a horseshoe shape and wherein the connecting member includes a bottom surface that forms a continuous plane with the bottom surface of the first member; and
a channel for circulating cooling fluid through the first and second members.

30. The stabilizer of claim 29, wherein the first and second members are elongate and generally parallel to each other.

31. A method for stabilizing a predetermined area of body tissue to perform a surgical operation, comprising steps of:
attaching a cooled stabilizer comprising a first member having an insulated upper surface and a thermally conductive bottom surface; a second member having an insulated upper surface and a thermally conductive bottom surface; an interconnecting member interconnecting the first member and the second member, wherein the first member, second member and interconnecting member are in a horseshoe shape and wherein the interconnecting member includes a bottom surface that forms a continuous plane with the bottom surface of the first member and a cooling channel for circulating cooling fluid through the first and second member to an arm;
positioning the arm along a retractor;
circulating cooling fluid through the cooled stabilizer; and arranging the cooled stabilizer over the predetermined area of body tissue.

32. The method of claim 31, and further including a step of circulating fluid having a temperature greater than the cooling fluid to remove the stabilizer from the predetermined area.

33. The method of claim 31, and further including steps of attaching flexible tapes to the cooled stabilizer and threading the tapes through tissue adjacent the predetermined area to reduce movement of the adjacent tissue.

34. The method of claim 31, wherein the cooling fluid has a temperature of between approximately −30° C. and 10° C.

35. The method of claim 31, wherein the cooling fluid has a temperature of between approximately −20° C. and 0° C.

36. The method of claim 31, wherein the cooling fluid has a temperature of between approximately −10° C. and 0° C.

37. The method of claim 31, wherein the cooling fluid is a saline solution.

38. The method of claim 31, wherein the cooling fluid is a saline/alcohol solution.

39. The method of claim 31, wherein the cooled stabilizer includes a pad to provide traction in the predetermined area.

40. The method of claim 31, wherein while the cooled stabilizer is arranged on the predetermined area, it can provide traction and quiescence in the predetermined area.

41. The method of claim 31, further including the step of drying the tissue along the predetermined area of body tissue.

* * * * *